US006677347B2

(12) United States Patent
Crooks et al.

(10) Patent No.: US 6,677,347 B2
(45) Date of Patent: Jan. 13, 2004

(54) SULFONAMIDO ETHER SUBSTITUTED IMIDAZOQUINOLINES

(75) Inventors: Stephen L. Crooks, Mahtomedi, MN (US); George W. Griesgraber, Eagan, MN (US); Philip D. Heppner, Woodbury, MN (US); Bryon A. Merrill, River Falls, WI (US); Ralph R. Roberts, Cottage Grove, MN (US); Ai-Ping Wei, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/165,443

(22) Filed: Jun. 7, 2002

(65) Prior Publication Data

US 2003/0139441 A1 Jul. 24, 2003

Related U.S. Application Data

(63) Continuation-in-part of application No. 10/012,599, filed on Dec. 1, 2001.
(60) Provisional application No. 60/254,218, filed on Dec. 8, 2000.

(51) Int. Cl.[7] ................... A61K 31/4745; A61P 37/02; A61P 31/12; C07D 471/04

(52) U.S. Cl. ................... 514/293; 546/82; 546/84; 546/159

(58) Field of Search ............... 546/82, 159, 84; 514/293

(56) References Cited

U.S. PATENT DOCUMENTS

| 3,314,941 | A | 4/1967 | Littell et al. |
| 4,689,338 | A | 8/1987 | Gerster |
| 4,698,348 | A | 10/1987 | Gerster |
| 4,929,624 | A | 5/1990 | Gerster et al. |
| 4,988,815 | A | 1/1991 | Andre et al. |
| 5,037,986 | A | 8/1991 | Gerster |
| 5,175,296 | A | 12/1992 | Gerster |
| 5,238,944 | A | 8/1993 | Wick et al. |
| 5,266,575 | A | 11/1993 | Gerster |
| 5,268,376 | A | 12/1993 | Gester |
| 5,346,905 | A | 9/1994 | Gerster |
| 5,352,784 | A | 10/1994 | Nikolaides et al. |
| 5,367,076 | A | 11/1994 | Gerster |
| 5,389,640 | A | 2/1995 | Gerster et al. |
| 5,395,937 | A | 3/1995 | Nikolaides et al. |
| 5,446,153 | A | 8/1995 | Lindstrom et al. |
| 5,482,936 | A | 1/1996 | Lindstrom |
| 5,693,811 | A | 12/1997 | Lindstrom |
| 5,741,908 | A | 4/1998 | Gerster et al. |
| 5,756,747 | A | 5/1998 | Gerster |
| 5,939,090 | A | 8/1999 | Beaurline et al. |
| 6,039,969 | A | 3/2000 | Tomai et al. |
| 6,069,149 | A | 5/2000 | Nanba et al. |
| 6,083,505 | A | 7/2000 | Miller et al. |
| 6,110,929 | A | 8/2000 | Gerster et al. |
| 6,194,425 | B1 | 2/2001 | Gerster et al. |
| 6,245,776 | B1 | 6/2001 | Skwierczynski et al. |
| 6,331,539 | B1 | 12/2001 | Crooks et al. |
| 6,376,669 | B1 | 4/2002 | Rice et al. |
| 2002/0055517 | A1 | 5/2002 | Smith |
| 2002/0058674 | A1 | 5/2002 | Hedenstrom et al. |

FOREIGN PATENT DOCUMENTS

| EP | 0 394 026 | 10/1990 |
| EP | 1 104 764 | 6/2001 |
| JP | 9-208584 | 8/1997 |
| JP | 9-255926 | 3/1999 |
| JP | 11-222432 | 8/1999 |
| JP | 2000-247884 | 9/2000 |
| WO | WO 00/47719 | 8/2000 |
| WO | WO 00/76505 | 12/2000 |
| WO | WO 00/76518 | 12/2000 |
| WO | WO 01/74343 | 10/2001 |
| WO | WO 02/36592 | 5/2002 |
| WO | WO 02/46188 | 6/2002 |
| WO | WO 02/46189 | 6/2002 |
| WO | WO 02/46190 | 6/2002 |
| WO | WO 02/46191 | 6/2002 |
| WO | WO 02/46192 | 6/2002 |
| WO | WO 02/46193 | 6/2002 |
| WO | WO 02/46194 | 6/2002 |
| WO | WO 02/46749 | 6/2002 |

OTHER PUBLICATIONS

Wozniak, et al, "The Amination of 3–nitro–1, 5–naphthyridines by Liquid Ammonia/Potassium Permanganate[1,2]. A New and Convenient Amination Method.", *Journal of the Royal Netherlands Chemical Society*, 102, pp 511–513, Dec. 12, 1983.

Brennan, et al, "Automated Bioassay of Interferons in Micro–test Plates", *Biotechniques*, Jun./Jul., 78, 1983.

Testerman, et al., "Cytokine Induction by the Immunomodulators Imiquimod and S–27609", *Journal of Leukocyte Biology*, vol. 58, pp. 365–372, Sep. 1995.

Bachman, et al, "Synthesis of Substituted Quinolylamines. Derivatives of 4–Amino–7–Chloroquinoline", *J. Org. Chem*, 15, pp 1278–1284 (1950).

Jain, et al, "Chemical and Pharmacological Investigations of Some ω–Substituted Alkylamino–3–aminopyridines", *J. Med. Chem.*, 11, pp 87–92 (1968).

Baranov, et al., *Chem. Abs.* 85, 94371, (1976).

Berényi, et al, "Ring Transformation of Condensed Dihydro–as–triazines", *J. Heterocyclic Chem.*, 18, pp 1537–1540 (1981).

Chollet, et al, "Development of a Topically Active Imiquimod Formulation", *Pharmaceutical Development and Technology*, 4(1), pp 35–43 (1999).

*Primary Examiner*—Evelyn Mei Huang
(74) *Attorney, Agent, or Firm*—Dean A. Ersfeld

(57) ABSTRACT

Imidazoquinoline and tetrahydroimidazoquinoline compounds that contain ether and sulfonamide or sulfamide functionality at the 1-position are useful as immune response modifiers. The compounds and compositions of the invention can induce the biosynthesis of various cytokines and are useful in the treatment of a variety of conditions including viral diseases and neoplastic diseases.

26 Claims, No Drawings

SULFONAMIDO ETHER SUBSTITUTED IMIDAZOQUINOLINES

This application is a continuation-in-part of U.S. Ser. No. 10/012,599, filed on Dec. 1, 2001, which claims the benefit of previously filed Provisional Application Serial No. 60/254,218, filed on Dec. 8, 2000.

FIELD OF THE INVENTION

This invention relates to imidazoquinoline compounds that have ether and sulfonamide or sulfamide functionality at the 1-position, and to pharmaceutical compositions containing such compounds. The invention also provides methods of making the compounds and intermediates useful in their synthesis. A further aspect of this invention relates to the use of these compounds as immunomodulators, for inducing cytokine biosynthesis in animals, and in the treatment of diseases, including viral and neoplastic diseases.

BACKGROUND OF THE INVENTION

The first reliable report on the 1H-imidazo[4,5-c] quinoline ring system, Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c] quinolines were reported. For example, Jain et al., *J. Med. Chem.* 11, pp. 87–92 (1968), synthesized the compound 1-[2-(4-piperidyl)ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo[4,5-c]quinolines, and Berenyi et al., *J. Heterocyclic Chem.* 18, 1537–1540 (1981), have reported certain 2-oxoimidazo[4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640, all of which are incorporated herein by reference. There continues to be interest in the imidazoquinoline ring system. Certain 1H-imidazo[4,5-c] naphthyridine-4-amines, 1H-imidazo [4,5-c] pyridin-4-amines, and 1H-imidazo[4,5-c] quinolin-4-amines having an ether containing substituent at the 1 position are known. These are described in U.S. Pat. Nos. 5,268,376; 5,389,640; 5,494,916; and WO 99/29693.

There is a continuing need for compounds that have the ability to modulate the immune response, by induction of cytokine biosynthesis or other mechanisms.

SUMMARY OF THE INVENTION

We have found a new class of compounds that are useful in inducing cytokine biosynthesis in animals. Accordingly, this invention provides imidazoquinoline-4-amine and tetrahydroimidazoquinoline-4-amine compounds that have an ether and sulfonamide or sulfamide containing substituent at the 1-position. The compounds are defined by Formulas (I) and (II), which are defined in more detail infra. These compounds share the general structural formula

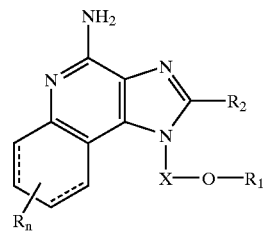

wherein X, $R_1$, $R_2$, and R are as defined herein for each class of compounds having Formulas (I) and (II).

The compounds of Formulas (I) and (II) are useful as immune response modifiers due to their ability to induce cytokine biosynthesis and otherwise modulate the immune response when administered to animals. This makes the compounds useful in the treatment of a variety of conditions such as viral diseases and tumors that are responsive to such changes in the immune response.

The invention further provides pharmaceutical compositions containing the immune response modifying compounds, and methods of inducing cytokine biosynthesis in an animal, treating a viral infection in an animal, and/or treating a neoplastic disease in an animal by administering a compound of Formula (I) or (II) to the animal.

In addition, the invention provides methods of synthesizing the compounds of the invention and novel intermediates useful in the synthesis of these compounds.

DETAILED DESCRIPTION OF THE INVENTION

As mentioned earlier, we have found certain compounds that induce cytokine biosynthesis and modify the immune response in animals. Such compounds are represented by Formulas (I) and (II), shown below.

Imidazoquinoline compounds of the invention, which have ether and sulfonamide or sulfamide functionality at the 1-position are represented by Formula (I):

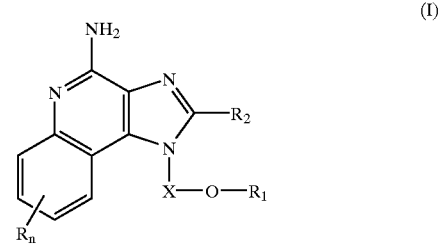

wherein:
  X is —$CHR_5$—, —$CHR_5$-alkyl-, or —$CHR_5$-alkenyl-;
  $R_1$ is selected from the group consisting of:
    —$R_4$—$NR_3$—$SO_2$—$R_6$-alkyl;
    —$R_4$—$NR_3$—$SO_2$—$R_6$-alkenyl;
    —$R_4$—$NR_3$—$SO_2$—$R_6$-aryl;
    —$R_4$—$NR_3$—$SO_2$—$R_6$-heteroaryl;
    —$R_4$—$NR_3$—$SO_2$—$R_6$-heterocyclyl;
    —$R_4$—$NR_3$—$SO_2$—$R_7$;
    —$R_4$—$NR_3$—$SO_2$—$NR_5$—$R_6$-alkyl;
    —$R_4$—$NR_3$—$SO_2$—$NR_5$—$R_6$-alkenyl;
    —$R_4$—$NR_3$—$SO_2$—$NR_5$—$R_6$-aryl;
    —$R_4$—$NR_3$—$SO_2$—$NR_5$—$R_6$-heteroaryl;
    —$R_4$—$NR_3$—$SO_2$—$NR_5$—$R_6$-heterocyclyl; and
    —$R_4$—$NR_3$—$SO_2$—$NH_2$;

$R_2$ is selected from the group consisting of:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from the group consisting of:
  - —OH;
  - -halogen;
  - —N($R_5$)$_2$;
  - —CO—N($R_5$)$_2$;
  - —CO—$C_{1-10}$ alkyl;
  - —CO—O—$C_{1-10}$ alkyl;
  - —$N_3$;
  - -aryl;
  - -heteroaryl;
  - -heterocyclyl;
  - —CO-aryl; and
  - —CO-heteroaryl;

Y is —O— or —S(O)$_{0-2}$—;

$R_3$ is H, $C_{1-10}$ alkyl, or arylalkyl;

$R_4$ is alkyl or alkenyl, which may be interrupted by one or more —O— groups; or $R_3$ and $R_4$ can join together to form a ring;

each $R_5$ is independently H, $C_{1-10}$ alkyl, or $C_{2-10}$ alkenyl;

$R_6$ is a bond, alkyl, or alkenyl, which may be interrupted by one or more —O— groups;

$R_7$ is $C_{1-10}$ alkyl; or $R_3$ and $R_7$ can join together to form a ring;

n is 0 to 4; and each R present is independently selected from the group consisting of $C_{1-10}$ alkyl, $C_{1-10}$ alkoxy, hydroxy, halogen and trifluoromethyl;

or a pharmaceutically acceptable salt thereof.

The invention also includes tetrahydroimidazoquinoline compounds that bear an ether and sulfanomide or sulfamide containing substituent at the 1-position. Such tetrahydroimidazoquinoline compounds are represented by Formula (II):

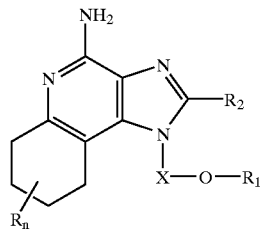

(II)

wherein:

X is —CHR$_5$—, —CHR$_5$-alkyl-, or —CHR$_5$-alkenyl-;

$R_1$ is selected from the group consisting of:
- —$R_4$—$NR_3$—$SO_2$—$R_6$-alkyl;
- —$R_4$—$NR_3$—$SO_2$—$R_6$-alkenyl;
- —$R_4$—$NR_3$—$SO_2$—$R_6$-aryl;
- —$R_4$—$NR_3$—$SO_2$—$R_6$-heteroaryl;
- —$R_4$—$NR_3$—$SO_2$—$R_6$-heterocyclyl;
- —$R_4$—$NR_3$—$SO_2$—$R_7$;
- —$R_4$—$NR_3$—$SO_2$—$NR_5$—$R_6$-alkyl;
- —$R_4$—$NR_3$—$SO_2$—$NR_5$—$R_6$-alkenyl;
- —$R_4$—$NR_3$—$SO_2$—$NR_5$—$R_6$-aryl;
- —$R_4$—$NR_3$—$SO_2$—$NR_5$—$R_6$-heteroaryl;
- —$R_4$—$NR_3$—$SO_2$—$NR_5$—$R_6$-heterocyclyl; and
- —$R_4$—$NR_3$—$SO_2$—$NH_2$;

$R_2$ is selected from the group consisting of:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from the group consisting of:
  - —OH;
  - -halogen;
  - —N($R_5$)$_2$;
  - —CO—N($R_5$)$_2$;
  - —CO—$C_{1-10}$ alkyl;
  - —CO—O—$C_{1-10}$ alkyl;
  - —$N_3$;
  - -aryl;
  - -heteroaryl;
  - -heterocyclyl;
  - —CO-aryl; and
  - —CO-heteroaryl;

Y is —O— or —S(O)$_{0-2}$—;

$R_3$ is H, $C_{1-10}$ alkyl, or arylalkyl;

$R_4$ is alkyl or alkenyl, which may be interrupted by one or more —O— groups; or $R_3$ and $R_4$ can join together to form a ring;

each $R_5$ is independently H, $C_{1-10}$ alkyl, or $C_{2-10}$ alkenyl;

$R_6$ is a bond, alkyl, or alkenyl, which may be interrupted by one or more —O— groups;

$R_7$ is $C_{1-10}$ alkyl; or $R_3$ and $R_7$ can join together to form a ring;

n is 0 to 4; and each R present is independently selected from the group consisting of $C_{1-10}$ alkyl, $C_{1-10}$ alkoxy, hydroxy, halogen, and trifluoromethyl;

or a pharmaceutically acceptable salt thereof.

Preparation of the Compounds

Compounds of the invention can be prepared according to Reaction Scheme I where R, $R_1$, $R_2$, X and n are as defined above.

In step (1) of Reaction Scheme I a 2,4-dichloro-3-nitroquinoline of Formula X is reacted with an amine of Formula $R_1$—O—X—$NH_2$ to provide a 2-chloro-3-nitroquinolin-4-amine of Formula XI. The reaction can be carried out by adding the amine to a solution of a compound of Formula X in a suitable solvent such as chloroform or dichloromethane and optionally heating. Many quinolines of Formula XI are known or can be prepared using known synthetic methods, see for example, Andre et al., U.S. Pat. No. 4,988,815 and references cited therein. Many amines of Formula $R_1$—O—X—$NH_2$ are known; some are commercially available and others can by prepared using known synthetic methods.

In step (2) of Reaction Scheme I a 2-chloro-3-nitroquinolin-4-amine of Formula XI is reduced to provide a 2-chloroquinoline-3,4-diamine of Formula XII. Preferably, the reduction is carried out using a conventional heterogeneous hydrogenation catalyst such as platinum on carbon or palladium on carbon. The reaction can conveniently be carried out on a Parr apparatus in a suitable solvent such as ethanol, isopropanol or toluene.

tion is carried out by heating (e.g., 125–175° C.) a compound of Formula XIII under pressure in a sealed reactor in the presence of a solution of ammonia in an alkanol. The product or a pharmaceutically acceptable salt thereof can be isolated using conventional methods.

Reaction Scheme I

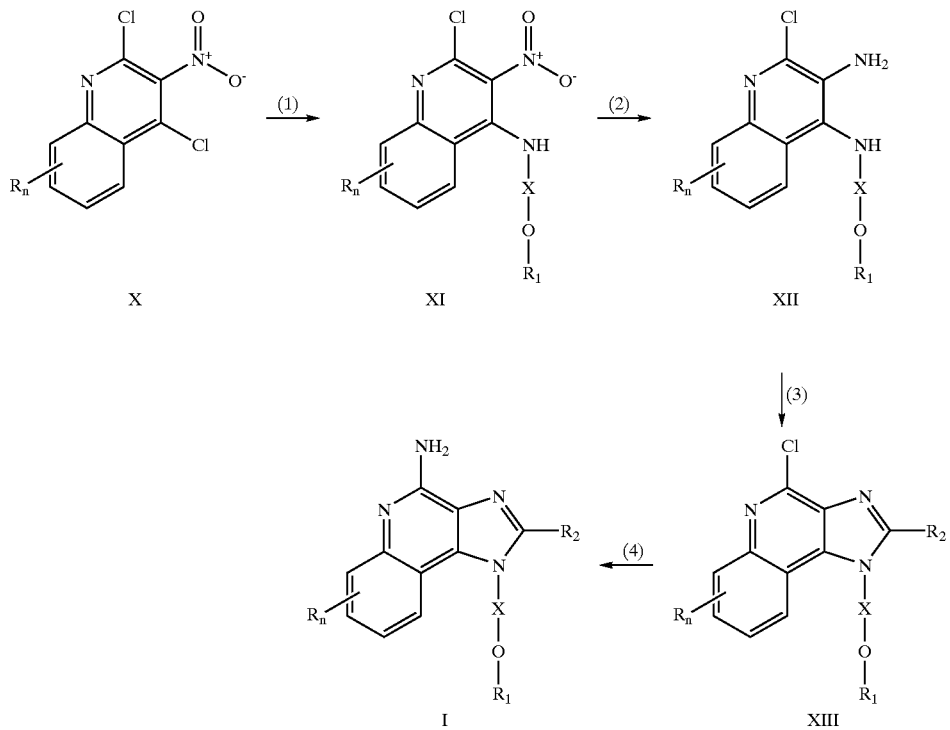

In step (3) of Reaction Scheme I a 2-chloroquinoline-3,4-diamine of Formula XII is reacted with a carboxylic acid or an equivalent thereof to provide a 4-chloro-1H-imidazo[4,5-c]quinoline of Formula XIII. Suitable equivalents to carboxylic acid include orthoesters and 1,1-dialkoxyalkyl alkanoates. The carboxylic acid or equivalent is selected such that it will provide the desired $R_2$ substituent in a compound of Formula XIII. For example, triethyl orthoformate will provide a compound where $R_2$ is hydrogen and triethyl orthoacetate will provide a compound where $R_2$ is methyl. The reaction can be run in the absence of solvent or in an inert solvent such as toluene. The reaction is run with sufficient heating to drive off any alcohol or water formed as a byproduct of the reaction.

Alternatively, step (3) can be carried out by (i) reacting the diamine of Formula XII with an acyl halide of Formula $R_2C(O)Cl$ and then (ii) cyclizing. In part (i) the acyl halide is added to a solution of the diamine in an inert solvent such as acetonitrile or dichloromethane. The reaction can be carried out at ambient temperature. The product can be isolated using conventional methods. In part (ii) the product of part (i) is heated in an alcoholic solvent in the presence of a base. Preferably the product of part (i) is refluxed in ethanol in the presence of an excess of triethylamine or heated with methanolic ammonia.

In step (4) of Reaction Scheme I a 4-chloro-1H-imidazo[4,5-c]quinoline of Formula XIII is aminated to provide a 1H-imidazo[4,5-c]quinolin-4-amine of Formula I. The reac- Compounds of the invention containing a sulfonamide group can be prepared according to Reaction Scheme II where R, $R_2$, $R_3$, $R_4$, X and n are as defined above, BOC is tert-butoxycarbonyl and $R_{11}$ is —$R_6$-alkyl, —$R_6$-aryl, —$R_6$-heteroaryl or —$R_6$-heterocyclyl where $R_6$ is as defined above.

In step (1) of Reaction Scheme II the amino group of an aminoalcohol of Formula XIV is protected with a tert-butoxycarbonyl group. A solution of the aminoalcohol in tetrahydrofuran is treated with di-tert-butyl dicarbonate in the presence of a base such as sodium hydroxide. Many aminoalcohols of Formula XIV are commercially available; others can be prepared using known synthetic methods.

In step (2) of Reaction Scheme II a protected aminoalcohol of Formula XV is converted to an iodide of Formula XVI. Iodine is added to a solution of triphenylphosphine and imidazole in dichloromethane; then a solution of a protected aminoalcohol of Formula XV in dichloromethane is added. The reaction is carried out at ambient temperature.

In step (3) of Reaction Scheme II a 1H-imidazo[4,5-c]quinolin-1-yl alcohol of Formula XVII is alkylated with an iodide of Formula XVI to provide a 1H-imidazo[4,5-c]quinolin-1-yl ether of Formula XVIII. The alcohol of Formula XVII is reacted with sodium hydride in a suitable solvent such as N,N-dimethylformamide to form an alkoxide. The iodide is added to the alkoxide solution at ambient temperature. After the addition is complete the reaction is stirred at an elevated temperature (~100° C.). Many compounds of Formula XVII are known, see for example, Gerster, U.S. Pat. No. 4,689,338; others can readily be prepared using known synthetic routes, see for example, Gerster et al., U.S. Pat. No. 5,605,899 and Gerster, U.S. Pat. No. 5,175,296.

In step (4) of Reaction Scheme II a 1H-imidazo[4,5-c]quinolin-1-yl ether of Formula XVIII is oxidized to provide a 1H-imidazo[4,5-c]quinoline-5N-oxide of Formula XIX using a conventional oxidizing agent capable of forming N-oxides. Preferably a solution of a compound of Formula XVIII in chloroform is oxidized using 3-chloroperoxybenzoic acid at ambient temperature.

In step (5) of Reaction Scheme II a 1H-imidazo[4,5-c]quinoline-5N-oxide of Formula XIX is aminated to provide a 1H-imidazo[4,5-c]quinolin-4-amine of Formula XX. Step (5) involves (i) reacting a compound of Formula XIX with an acylating agent and then (ii) reacting the product with an aminating agent. Part (i) of step (5) involves reacting an N-oxide of Formula XIX with an acylating agent. Suitable acylating agents include alkyl- or arylsulfonyl chlorides (e.g., benezenesulfonyl chloride, methanesulfonyl chloride, p-toluenesulfonyl chloride). Arylsulfonyl chlorides are preferred. Para-toluenesulfonyl chloride is most preferred. Part (ii) of step (5) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, ammonium phosphate). Ammonium hydroxide is preferred. The reaction is preferably carried out by dissolving the N-oxide of Formula XIX in an inert solvent such as dichloromethane or 1,2-dichloroethane with heating if necessary, adding the aminating agent to the solution, and then slowly adding the acylating agent. Optionally the reaction can be carried out in a sealed pressure vessel at an elevated temperature (85–100° C.).

In step (6) of Reaction Scheme II the protecting group is removed by hydrolysis under acidic conditions to provide a 1H-imidazo[4,5-c]quinolin-4-amine of Formula XXI. Preferably the compound of Formula XX is treated with hydrochloric acid/ethanol at ambient temperature or with gentle heating.

In step (7) of Reaction Scheme II a 1H-imidazo[4,5-c]quinolin-4-amine of Formula XXI is converted to a sulfonamide of Formula XXII which is a subgenus of Formula I using conventional synthetic methods. For example, a compound of Formula XXI can be reacted with a sulfonyl chloride of Formula $R_{11}S(O_2)Cl$. The reaction can be carried out by adding a solution of the sulfonyl chloride in a suitable solvent such as dichloromethane or 1-methyl-2-pyrrolidinone to a solution of a compound of Formula XXI at ambient temperature. Alternatively, a compound of Formula XXI can be reacted with a sulfonic anhydride of Formula $R_{11}S(O_2)OS(O_2)R_{11}$. The reaction can be run at ambient temperature in an inert solvent such as dichloromethane in the presence of a base such as pyridine or N,N-diisopropylethylamine. The product or a pharmaceutically acceptable salt thereof can be isolated using conventional methods.

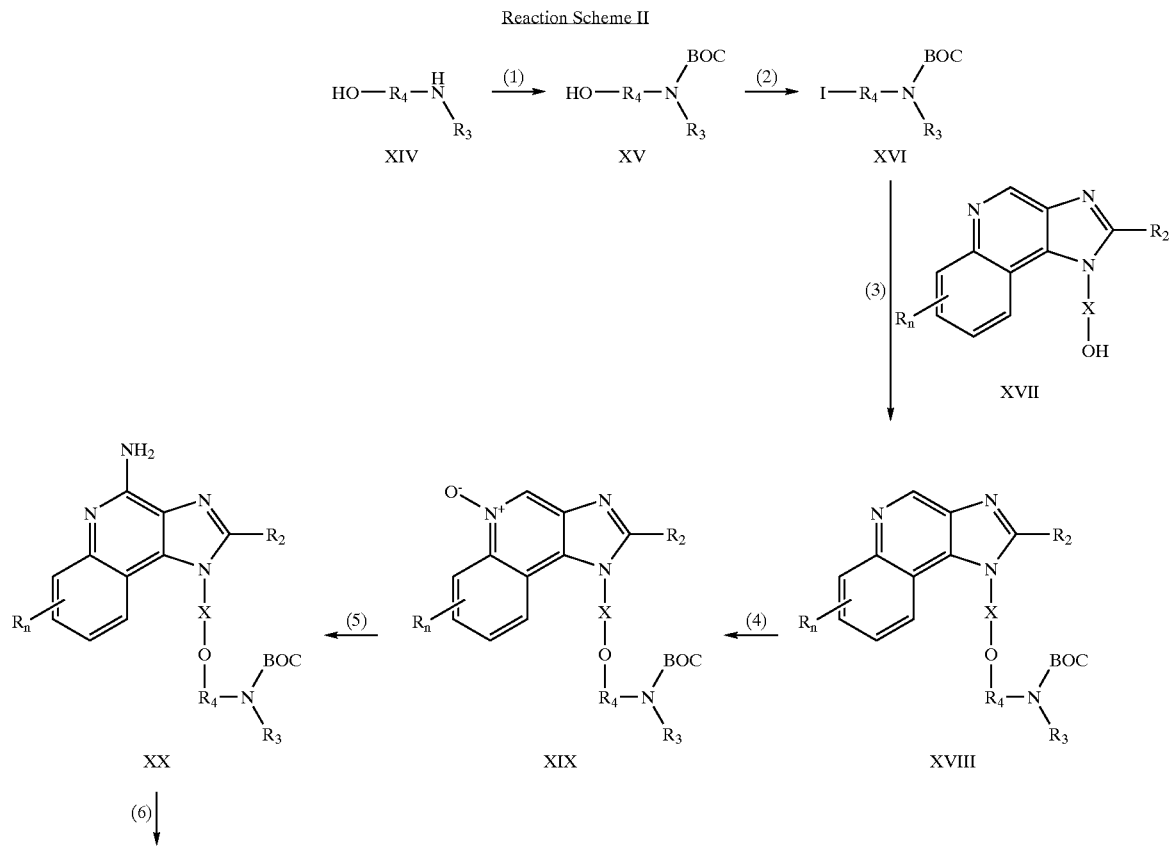

Reaction Scheme II

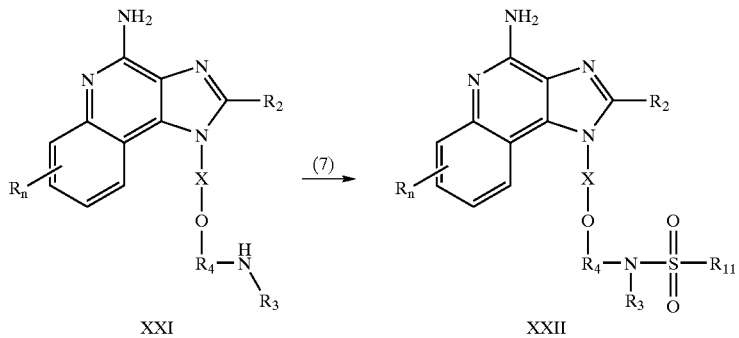

Compounds of the invention containing a sulfonamide group can be prepared according to Reaction Scheme III where R, $R_2$, $R_3$, $R_4$, $R_{11}$, X and n are as defined above and BOC is tert-butoxycarbonyl.

In step (1) of Reaction Scheme III the amino group of an aminoalcohol of Formula XXIII is protected with a tert-butoxycarbonyl group. A solution of the aminoalcohol in tetrahydrofuran is treated with di-tert-butyl dicarbonate in the presence of a base such as sodium hydroxide. Many aminoalcohols of Formula XXIII are commercially available; others can be prepared using known synthetic methods.

In step (2) of Reaction Scheme III a protected amino alcohol of Formula XXIV is converted to a methanesulfonate of Formula XXV. A solution of a compound of Formula XXIV in a suitable solvent such as dichloromethane is treated with methanesulfonyl chloride in the presence of a base such as triethylamine. The reaction can be carried out at a reduced temperature (0° C.).

In step (3a) of Reaction Scheme III a methanesulfonate of Formula XXV is converted to an azide of Formula XXVI. Sodium azide is added to a solution of a compound of Formula XXV in a suitable solvent such as N,N-dimethylformamide or tetrahydrofuran. The reaction can be carried out at an elevated temperature (80–100° C.).

In step (3b) of Reaction Scheme III a compound of Formula XXVI is alkylated with a halide of Formula Hal-$R_3$ to provide a compound of Formula XXVII. In compounds where $R_3$ is hydrogen this step is omitted. The compound of Formula XXVI is reacted with sodium hydride in a suitable solvent such as N,N-dimethylformamide to form the anion and then combined with the halide. The reaction can be carried out at ambient temperature.

In step (4) of Reaction Scheme III an azide of Formula XXVI or XXVII is reduced to provide an amine of Formula XXVIII. Preferably, the reduction is carried out using a conventional heterogeneous hydrogenation catalyst such as palladium on carbon. The reaction can conveniently be carried out on a Parr apparatus in a suitable solvent such as methanol or isopropanol.

In step (5) of Reaction Scheme III a 4-chloro-3-nitroquinoline of Formula XXIX is reacted with an amine of Formula XXVIII to provide a 3-nitroquinoline of Formula XXX. The reaction can be carried out by adding an amine of Formula XXVIII to a solution of a compound of Formula XXIX in a suitable solvent such as dichloromethane in the presence of a base such as triethylamine. Many quinolines of Formula XXIX are known compounds or can be prepared using known synthetic methods, see for example, U.S. Pat. No. 4,689,338 and references cited therein.

In step (6) of Reaction Scheme III a 3-nitroquinoline of Formula XXX is reduced to provide a 3-aminoquinoline of Formula XXXI. Preferably, the reduction is carried out using a conventional heterogeneous hydrogenation catalyst such as platinum on carbon. The reaction can conveniently be carried out on a Parr apparatus in a suitable solvent such as toluene.

In step (7) of Reaction Scheme III a compound of Formula XXXI is reacted with a carboxylic acid or an equivalent thereof to provide a 1H-imidazo[4,5-c]quinoline of Formula XVIII. Suitable equivalents to carboxylic acid include orthoesters, and 1,1-dialkoxyalkyl alkanoates. The carboxylic acid or equivalent is selected such that it will provide the desired $R_2$ substituent in a compound of Formula XVIII. For example, triethyl orthoformate will provide a compound where $R_2$ is hydrogen and triethyl orthovalerate will provide a compound where $R_2$ is butyl. The reaction can be run in the absence of solvent or in an inert solvent such as toluene. The reaction is run with sufficient heating to drive off any alcohol or water formed as a byproduct of the reaction. Optionally a catalytic amount of pyridine hydrochloride can be included.

Alternatively, step (7) can be carried out by (i) reacting a compound of Formula XXXI with an acyl halide of Formula $R_2C(O)Cl$ and then (ii) cyclizing. In part (i) the acyl halide is added to a solution of a compound of Formula XXXI in an inert solvent such as acetonitrile or dichloromethane. The reaction can be carried out at ambient temperature or at a reduced temperature. In part (ii) the product of part (i) is heated in an alcoholic solvent in the presence of a base. Preferably the product of part (i) is refluxed in ethanol in the presence of an excess of triethylamine or heated with methanolic ammonia.

Steps (8), (9), (10) and (11) are carried out in the same manner as steps (4), (5), (6) and (7) of Reaction Scheme II.

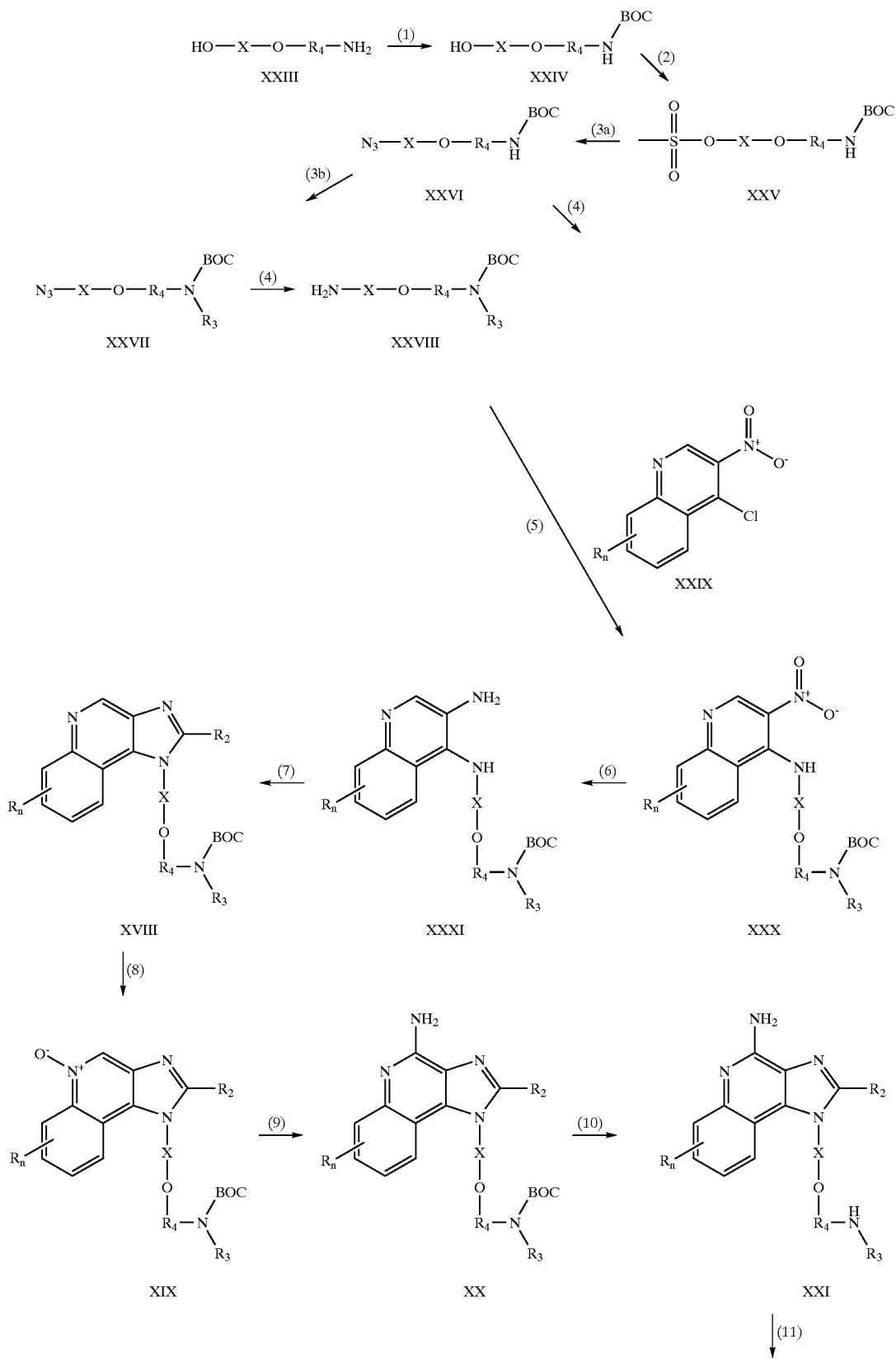

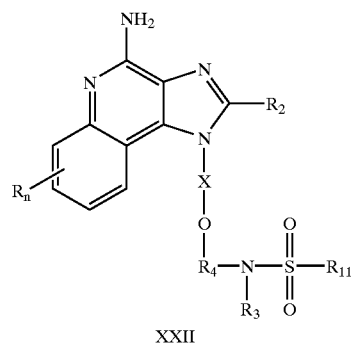

XXII

Compounds of the invention containing a sulfamide group can be prepared according to Reaction Scheme IV where R, $R_2$, $R_3$, $R_4$, $R_5$, $R_{11}$, X and n are as defined above.

In step (1) of Reaction Scheme IV a 1H-imidazo[4,5-c]quinolin-4-amine of Formula XXI is reacted with sulfuryl chloride to generate in situ a sulfamoyl chloride of Formula XXXII. The reaction can be carried out by adding a solution of sulfuryl chloride in dichloromethane to a solution of a compound of Formula XXI in dichloromethane in the presence of 1 equivalent of 4-(dimethylamino)pyridine. The reaction is preferably carried out at a reduced temperature (−78° C.).

In step (2) of Reaction Scheme IV an amine of Formula $HNR_5R_{11}$ is reacted with the sulfamoyl chloride of Formula XXXII to provide a sulfamide of Formula XXXIII which is a subgenus of Formula I. The reaction can be carried out by adding a solution containing 2 equivalents of the amine and 2 equivalents of triethylamine in dichloromethane to the reaction mixture from step (1). The addition is preferably carried out at a reduced temperature (−78° C.). After the addition is complete the reaction mixture can be allowed to warm to ambient temperature. The product or a pharmaceutically acceptable salt thereof can be isolated using conventional methods.

Reaction Scheme IV

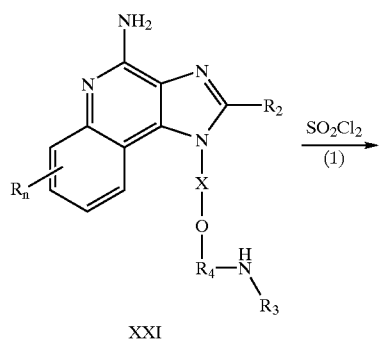

XXI

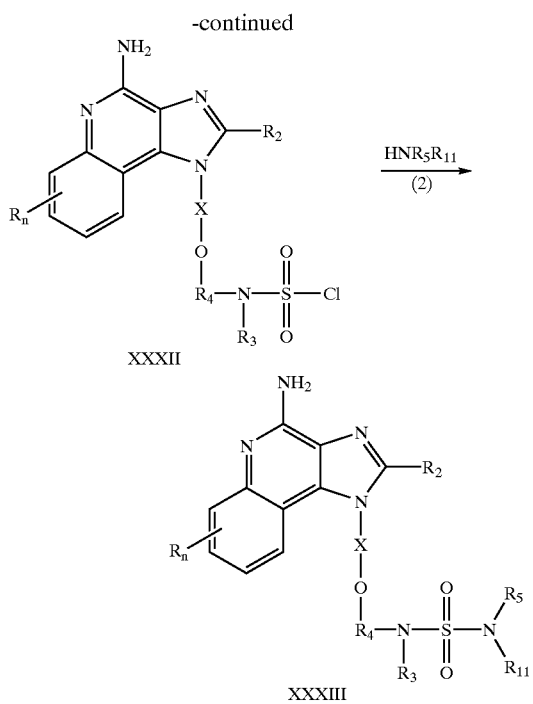

Compounds of the invention can be prepared according to Reaction Scheme V where R, $R_2$, $R_3$, $R_4$, $R_{11}$, X and n are as defined above.

In step (1) of Reaction Scheme V a 1H-imidazo[4,5-c]quinolin-4-amine of Formula XXI is reduced to provide a 6,7,8,9-tetrahydro-1H-imidazo[4,5-c]quinolin-4-amine of Formula XXXIV. Preferably the reduction is carried out by suspending or dissolving a compound of Formula XXI in trifluoroacetic acid, adding a catalytic amount of platinum (IV) oxide, and then hydrogenating. The reaction can be conveniently carried out in a Parr apparatus.

Step (2) is carried out in the same manner as step (7) of Reaction Scheme II to provide a 6,7,8,9-tetrahydro-1H-imidazo[4,5-c]quinolin-4-amine of Formula XXXV which is a subgenus of Formula II. The product or a pharmaceutically acceptable salt thereof can be isolated using conventional methods.

Reaction Scheme V

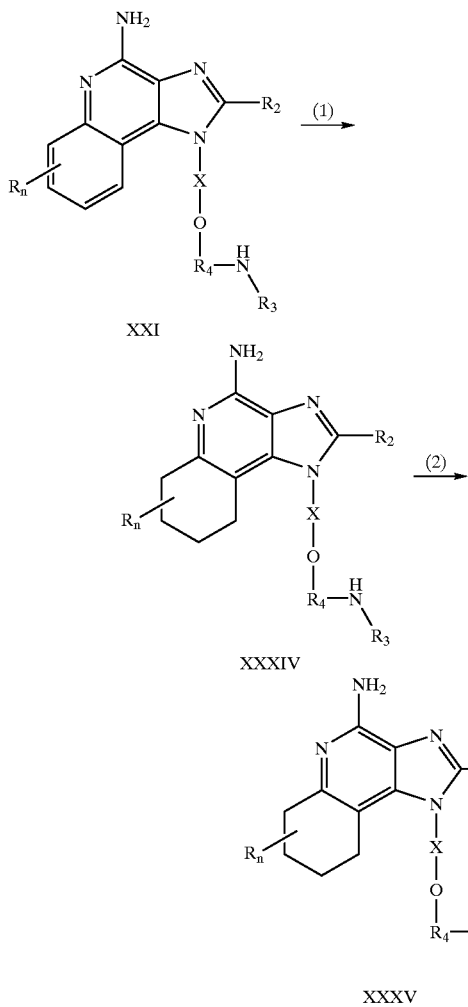

Reaction Scheme VI

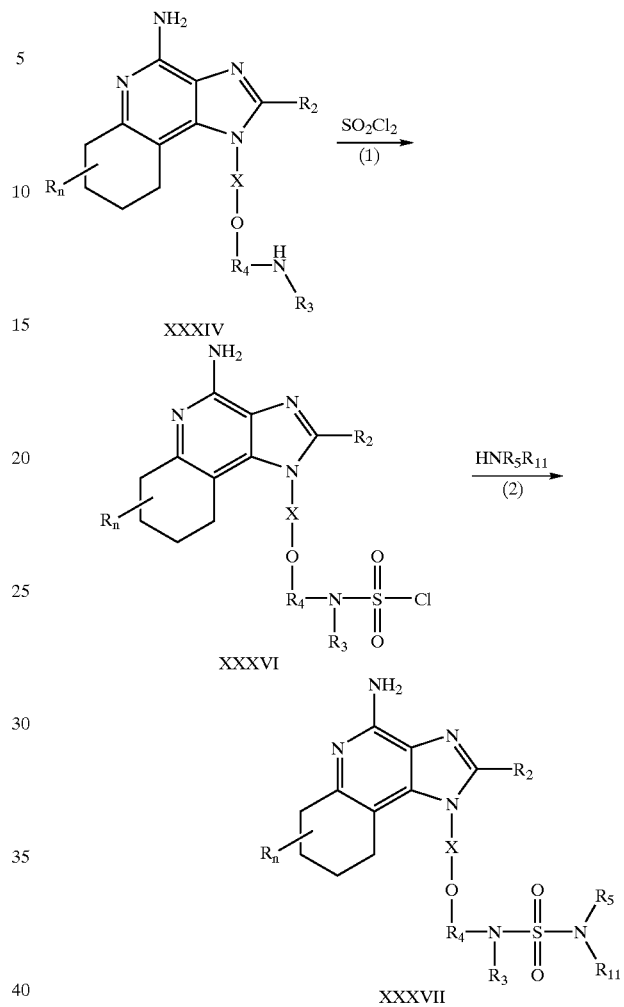

Compounds of the invention containing a sulfamide group can be prepared according to Reaction Scheme VI where R, $R_2$, $R_3$, $R_4$, $R_5$, $R_{11}$, X and n are as defined above.

In step (1) of Reaction Scheme VI a 1H-imidazo[4,5-c] quinolin-4-amine of Formula XXXIV is reacted with sulfuryl chloride to generate in situ a sulfamoyl chloride of Formula XXXVI. The reaction can be carried out by adding a solution of sulfuryl chloride in dichloromethane to a solution of a compound of Formula XXXIV in dichloromethane in the presence of 1 equivalent of 4-(dimethylamino)pyridine. The reaction is preferably carried out at a reduced temperature (−78° C.).

In step (2) of Reaction Scheme VI an amine of Formula $HNR_5R_{11}$ is reacted with the sulfamoyl chloride of Formula XXXVI to provide a sulfamide of Formula XXXVII which is a subgenus of Formula II. The reaction can be carried out by adding a solution containing 2 equivalents of the amine and 2 equivalents of triethylamine in dichloromethane to the reaction mixture from step (1). The addition is preferably carried out at a reduced temperature (−78° C.). After the addition is complete the reaction mixture can be allowed to warm to ambient temperature. The product or a pharmaceutically acceptable salt thereof can be isolated using conventional methods.

The invention also provides novel compounds useful as intermediates in the synthesis of the compounds of Formulas (I) and (II). These intermediate compounds have the structural Formula (III).

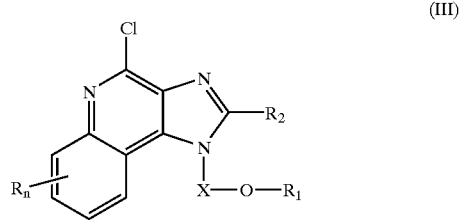

(III)

wherein X is —$CHR_5$—, —$CHR_5$-alkyl-, or —$CHR_5$-alkenyl-;

$R_1$ is selected from the group consisting of:
—$R_4$—$NR_3$—$SO_2$—$R_6$-alkyl;
—$R_4$—$NR_3$—$SO_2$—$R_6$-alkenyl;
—$R_4$—$NR_3$—$SO_2$—$R_6$-aryl;
—$R_4$—$NR_3$—$SO_2$—$R_6$-heteroaryl;
—$R_4$—$NR_3$—$SO_2$—$R_6$-heterocyclyl;
—$R_4$—$NR_3$—$SO_2$—$R_7$;
—$R_4$—$NR_3$—$SO_2$—$NR_5$—$R_6$-alkyl;
—$R_4$—$NR_3$—$SO_2$—$NR_5$—$R_6$-alkenyl;

—$R_4$—$NR_3$—$SO_2$—$NR_5$—$R_6$-aryl;
—$R_4$—$NR_3$—$SO_2$—$NR_5$—$R_6$-heteroaryl;
—$R_4$—$NR_3$—$SO_2$—$NR_5$—$R_6$-heterocyclyl;and
—$R_4$—$NR_3$—$SO_2$—$NH_2$;

$R_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—$N(R_5)_2$;
—CO—$N(R_5)_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;

Y is —O— or —$S(O)_{0-2}$—;

$R_3$ is H, $C_{1-10}$ alkyl, or arylalkyl;

$R_4$ is alkyl or alkenyl, which may be interrupted by one or more —O— groups; or $R_3$ and $R_4$ can join to form a ring;

each $R_5$ is independently H, $C_{1-10}$ alkyl, or $C_{2-10}$ alkenyl;

$R_6$ is a bond, or is alkyl or alkenyl, which may be interrupted by one or more —O— groups;

$R_7$ is $C_{1-10}$ alkyl; or $R_3$ and $R_7$ can join together to form a bond;

n is 0 to 4; and each R present is independently selected from the group consisting of $C_{1-10}$ alkyl, $C_{1-10}$ alkoxy, hydroxy, halogen and trifluoromethyl;

or a pharmaceutically acceptable salt thereof.

As used herein, the terms "alkyl", "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl and adamantyl.

In addition, the alkyl and alkenyl portions of —X— groups can be unsubstituted or substituted by one or more substituents, which substituents are selected from the groups consisting of alkyl, alkenyl, aryl, heteroaryl, heterocyclyl, arylalkyl, heteroarylalkyl, and heterocyclylalkyl.

The term "haloalkyl" is inclusive of groups that are substituted by one or more halogen atoms, including perfluorinated groups. This is also true of groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, quinoxalinyl, benzoimidazolyl, benzothiazolyl, naphthyridinyl, isoxazolyl, isothiazolyl, quinazolinyl, purinyl, and so on.

"Heterocyclyl" includes non-aromatic rings or ring systems that contain at least one ring hetero atom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, and the like.

The aryl, heteroaryl, and heterocyclyl groups can be unsubstituted or substituted by one or more substituents independently selected from the group consisting of alkyl, alkoxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylthio, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, arylcarbonyloxy, arylcarbonylthio, arylcarbonylamino, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylcarbonylamino and, in the case of heterocyclyl, oxo. If any other groups are identified as being "substituted" or "optionally substituted", then those groups can also be substituted by one or more of the above enumerated substituents.

Certain substituents are generally preferred. For example, preferred $R_1$ groups include —$R_4$—$NR_3$—$SO_2$—$R_6$-alkyl, —$R_4$—$NR_3$—$SO_2$—$R_6$-aryl, and —$R_4$—$NR_3$—$SO_2$—$R_6$-heteroaryl wherein the alkyl, aryl and heteroaryl groups can be unsubstituted or substituted and $R_4$ is preferably ethylene or n-butylene. Thiophene and quinoline are preferred heteroaryl groups Preferably no R substituents are present (i.e., n is 0). Preferred $R_2$ groups include hydrogen, alkyl groups having 1 to 4 carbon atoms (i.e., methyl, ethyl, propyl, isopropyl, n-butyl, sec-butyl, isobutyl, and cyclopropylmethyl), methoxyethyl, and ethoxymethyl. For substituted groups such as substituted alkyl or substituted aryl groups, preferred substituents include halogen, nitrile, methoxy, trifluoromethyl, and trifluoromethoxy. One or more of these preferred substituents, if present, can be present in the compounds of the invention in any combination.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers.

Pharmaceutical Compositions and Biological Activity

Pharmaceutical compositions of the invention contain a therapeutically effective amount of a compound of the invention as described above in combination with a pharmaceutically acceptable carrier.

The term "a therapeutically effective amount" means an amount of the compound sufficient to induce a therapeutic effect, such as cytokine induction, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 ng/kg to about 50 mg/kg, preferably about 10 μg/kg to about 5 mg/kg, of the compound to the subject. Any of the conventional dosage forms may be used, such as tablets, lozenges, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, etc.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and tumors. Accordingly, the invention provides a method of inducing cytokine biosynthesis in an animal comprising administering an effective amount of a compound or composition of the invention to the animal.

Certain compounds of the invention have been found to preferentially induce the expression of IFN-α in a population of hematopoietic cells such as PBMCs (peripheral blood mononuclear cells) containing pDC2 cells (precursor dendritic cell-type 2) without concomitant production of significant levels of inflammatory cytokines.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulates secretion of nitric oxide and the production of additional cytokines. Further, the compounds may cause proliferation and differentiation of B-lymphocytes.

Compounds of the invention also have an effect on the acquired immune response. For example, although there is not believed to be any direct effect on T cells or direct induction of T cell cytokines, the production of the T helper type 1 (Th1) cytokine IFN-γ is induced indirectly, and the production of the T helper type 2 (Th2) cytokines IL-4, IL-5 and IL-13 are inhibited upon administration of the compounds. This activity means that the compounds are useful in the treatment of diseases where upregulation of the Th1 response and/or downregulation of the Th2 response is desired. In view of the ability of compounds of the invention to inhibit the Th2 immune response, the compounds are expected to be useful in the treatment of atopic diseases, e.g., atopic dermatitis, asthma, allergy, allergic rhinitis; systemic lupus erythematosis; as a vaccine adjuvant for cell mediated immunity; and possibly as a treatment for recurrent fungal diseases and chlamydia.

The immune response modifying effects of the compounds make them useful in the treatment of a wide variety of conditions. Because of their ability to induce the production of cytokines such as IFN-α and/or TNF-α, the compounds are particularly useful in the treatment of viral diseases and tumors. This immunomodulating activity suggests that compounds of the invention are useful in treating diseases such as, but not limited to, viral diseases including genital warts; common warts; plantar warts; Hepatitis B; Hepatitis C; Herpes Simplex Virus Type I and Type II; molluscum contagiosum; variola, particularly variola major; HIV; CMV; VZV; rhinovirus; adenovirus; influenza; and para-influenza; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. pneumocystis carnii, cryptosporidiosis, histoplasmosis, toxoplasmosis, trypanosome infection, and leishmaniasis; and bacterial infections, e.g., tuberculosis, and mycobacterium avium. Additional diseases or conditions that can be treated using the compounds of the invention include actinic keratosis; eczema; eosinophilia; essential thrombocythaemia; leprosy; multiple sclerosis; Ommen's syndrome; discoid lupus; Bowen's disease; Bowenoid papulosis; alopecia areata; the inhibition of keloid formation after surgery and other types of post-surgical scars. In addition, these compounds could enhance or stimulate the healing of wounds, including chronic wounds. The compounds may be useful for treating the opportunistic infections and tumors that occur after suppression of cell mediated immunity in, for example, transplant patients, cancer patients and HIV patients.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to-about 50 mg/kg, preferably about 10 μg/kg to about 5 mg/kg. The invention also provides a method of treating a viral infection in an animal and a method of treating a neoplastic disease in an animal comprising administering an effective amount of a compound or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose of about 100 ng/kg to about 50 mg/kg, preferably about 10 µg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

The invention is further described by the following examples, which are provided for illustration only and are not intended to be limiting in any way.

In the examples below some of the compounds were purified using semi-preparative HPLC. A Waters Fraction Lynx automated purification system was used. The semi-prep HPLC fractions were analyzed using a Micromass LC-TOFMS and the appropriate fractions were combined and centrifuge evaporated to provide the trifluoroacetate salt of the desired compound.

Column: Phenomenex Luna C18(2), 10×50 mm, 5 micron particle size, 100 Å pore; flow rate: 25 mL/min.; gradient elution from 5–65% B in 4 min., then 65 to 95% B in 0.1 min., then hold at 95% B for 0.4 min., where A=0.05% trifluoroacetic acid/water and B=0.05% trifluoroacetic acid/acetonitrile; fraction collection by mass-selective triggering.

EXAMPLE 1

N-(2-{2-[4-amino-2-(2-methoxyethyl)-1H-imidazo[4,5-c]quinolin-1-yl]ethoxy}ethyl)methanesulfonamide

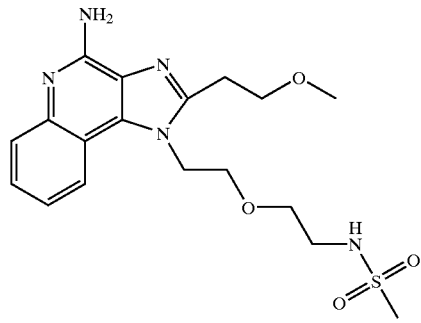

Part A

A solution of 2-(2-aminoethoxy)ethanol (29.0 g, 0.276 mol) in 180 mL of tetrahydrofuran (THF), under N₂, was cooled to 0° C. and treated with 140 mL of 2N NaOH solution. A solution of di-tert-butyl dicarbonate (60.2 g, 0.276 mol) in 180 mL of THF was then added dropwise over 1 h to the rapidly stirred solution. The reaction mixture was then allowed to warm to room temperature and was stirred an additional 18 h. The THF was then removed under reduced pressure and the remaining aqueous slurry was brought to pH 3 by addition of 150 mL of 1M H₂SO₄ solution. This was then extracted with ethyl acetate (300 mL, 100 mL) and the combined organic layers were washed with H₂O (2×) and brine. The organic portion was dried over Na₂SO₄ and concentrated to give tert-butyl 2-(2-hydroxyethoxy)ethylcarbamate as a colorless oil (47.1 g).

Part B

A rapidly stirred solution of tert-butyl 2-(2-hydroxyethoxy)ethylcarbamate (47.1 g, 0.230 mol) in 1 L of anhydrous CH₂Cl₂ was cooled to 0° C. under N₂ and treated with triethylamine (48.0 mL, 0.345 mol). Methanesulfonyl chloride (19.6 mL, 0.253 mol) was then added dropwise over 30 min. The reaction mixture was then allowed to warm to room temperature and was stirred an additional 22 h. The reaction was quenched by addition of 500 mL saturated NaHCO₃ solution and the organic layer was separated. The organic phase was then washed with H₂O (3×500 mL) and brine. The organic portion was dried over Na₂SO₄ and concentrated to give 2-{2-[(tert-butoxycarbonyl)amino]ethoxy}ethyl methanesulfonate as a brown oil (63.5 g).

Part C

A stirred solution of 2-{2-[(tert-butoxycarbonyl)amino]ethoxy}ethyl methanesulfonate (63.5 g, 0.224 mol) in 400 mL of N,N-dimethylformamide (DMF) was treated with NaN₃ (16.1 g, 0.247 mol) and the reaction mixture was heated to 90° C. under N₂. After 5 h, the solution was cooled to room temperature and treated with 500 mL of cold H₂O. The reaction-mixture was then extracted with Et₂O (3×300 mL). The combined organic extracts were washed with H₂O (4×100 mL) and brine (2×100 mL). The organic portion was dried over MgSO₄ and concentrated to give 52.0 g of tert-butyl 2-(2-azidoethoxy)ethylcarbamate as a light brown oil.

Part D

A solution of tert-butyl 2-(2-azidoethoxy)ethylcarbamate (47.0 g, 0.204 mol) in MeOH was treated with 4 g of 10% Pd on carbon and shaken under H₂ (3 Kg/cm²) for 24 h. The solution was then filtered through a Celite pad and concentrated to give 35.3 g of crude tert-butyl 2-(2-aminoethoxy)ethylcarbamate as a colorless liquid that was used without further purification.

Part E

A stirred solution of 4-chloro-3-nitroquinoline (31.4 g, 0.151 mol) in 500 mL of anhydrous CH₂Cl₂, under N₂, was treated with triethylamine (43 mL, 0.308 mol) and tert-butyl 2-(2-aminoethoxy)ethylcarbamate (0.151 mol). After stirring overnight, the reaction mixture was washed with H₂O (2×300 mL) and brine (300 mL). The organic portion was dried over Na₂SO₄ and concentrated to give a bright yellow solid. Recrystallization from ethyl acetate/hexanes gave 43.6 g of tert-butyl 2-{2-[(3-nitroquinolin-4-yl)amino]ethoxy}ethylcarbamate as bright yellow crystals.

Part F

A solution of tert-butyl 2-{2-[(3-nitroquinolin-4-yl)amino]ethoxy}ethylcarbamate (7.52 g, 20.0 mmol) in toluene was treated with 1.5 g of 5% Pt on carbon and shaken under H₂ (3 Kg/cm²) for 24 h. The solution was then filtered through a Celite pad and concentrated to give 6.92 g of crude tert-butyl 2-{2-[(3-aminoquinolin-4-yl)amino]ethoxy}ethylcarbamate as a yellow syrup.

Part G

A solution of tert-butyl 2-{2-[(3-aminoquinolin-4-yl)amino]ethoxy}ethylcarbamate (10.2 g, 29.5 mmol) in 250 mL of anhydrous CH₂Cl₂ was cooled to 0° C. and treated with triethylamine (4.18 mL, 30.0 mmol). Methoxypropionyl chloride (3.30 mL, 30.3 mmol) was then added dropwise over 5 min. The reaction was then warmed to room temperature and stirring was continued for 1 h. The reaction mixture was then concentrated under reduced pressure to give an orange solid. This was dissolved in 250 mL of EtOH and 12.5 mL of triethylamine was added. The mixture was heated to reflux and stirred under N₂ overnight. The reaction was then concentrated to dryness under reduced pressure and treated with 300 mL of Et₂O. The mixture was then filtered and the filtrate was concentrated under reduced pressure to give a brown solid. The solid was dissolved in 200 mL of hot MeOH and treated with activated charcoal. The hot solution was filtered and concentrated to give 11.1 g of tert-butyl 2-{2-[2-(2-methoxyethyl)-1H-imidazo[4,5-c]quinolin-1-yl]ethoxy}ethylcarbamate as a yellow syrup.

Part H

A solution of tert-butyl 2-{2-[2-(2-methoxyethyl)-1H-imidazo[4,5-c]quinolin-1-yl]ethoxy}ethylcarbamate (10.22 g, 24.7 mmol) in 250 mL of CHCl₃ was treated with 3-chloroperoxybenzoic acid (MCPBA, 77%, 9.12 g, 40.8 mmol). After stirring 30 min, the reaction mixture was washed with 1% Na₂CO₃ solution (2×75 mL) and brine. The organic layer was then dried over Na₂SO₄ and concentrated to give 10.6 g of tert-butyl 2-{2-[2-(2-methoxyethyl)-5-oxido-1H-imidazo[4,5-c]quinolin-1-yl]ethoxy}ethylcarbamate as an orange foam that was used without further purification.

Part I

A solution of tert-butyl 2-{2-[2-(2-methoxyethyl)-5-oxido-1H-imidazo[4,5-c]quinolin-1-yl]ethoxy}ethylcarbamate (10.6 g, 24.6 mmol) in 100 mL of 1,2-dichloroethane was heated to 60° C. and treated with 10 mL of concentrated NH₄OH solution. To the rapidly stirred solution was added solid p-toluenesulfonyl chloride (7.05 g, 37.0 mmol) over a 10 min period. The reaction mixture was treated with an additional 1 mL concentrated NH₄OH solution and then sealed in a pressure vessel and heating was continued for 2 h. The reaction mixture was then cooled and treated with 100 mL of CHCl₃. The reaction mixture was then washed with H₂O, 1% Na₂CO₃ solution (2×) and brine. The organic portion was dried over Na₂SO₄ and concentrated to give 10.6 g of tert-butyl 2-{2-[4-amino-2-(2-methoxyethyl)-1H-imidazo[4,5-c]quinolin 1-yl]ethoxy}ethylcarbamate as a brown foam.

Part J

Tert-butyl 2-{2-[4-amino-2-(2-methoxyethyl)-1H-imidazo[4,5-c]quinolin-1-yl]ethoxy}ethylcarbamate (10.6 g, 24.6 mmol) was treated with 75 mL of 2M HCl in EtOH and the mixture was heated to reflux with stirring. After 1.5 h, the reaction mixture was cooled and filtered to give a gummy solid. The solid was washed EtOH and Et₂O and dried under vacuum to give the hydrochloride salt as a light brown solid. The free base was made by dissolving the hydrochloride salt in 50 mL of H₂O and treating with 10% NaOH solution. The aqueous suspension was then concentrated to dryness and the residue was treated with CHCl₃. The resulting salts were removed by filtration and the filtrate was concentrated to give 3.82 g of 1-[2-(2-aminoethoxy)ethyl]-2-(2-methoxyethyl)-1H-imidazo[4,5-c]quinolin-4-amine as a tan powder.

MS 330 (M+H)⁺;

¹H NMR (300 MHz, DMSO-d₆) δ 8.10 (d, J=8.1 Hz, 1 H); 7.66 (d, J=8.2 Hz, 1H); 7.40 (m, 1 H); 7.25 (m, 1 H); 6.88 (br s, 2 H); 4.78 (t, J=5.4 Hz, 2 H); 3.89 (t, J=4.8 Hz, 2 H); 3.84 (t, J=6.9 Hz, 2 H); 3.54 (t, J=5.4 Hz, 2 H); 3.31 (s, 3 H); 3.23 (t, J=6.6 Hz, 2 H); 2.88 (t, J=5.3 Hz, 2 H).

Part K

1-[2-(2-Aminoethoxy)ethyl]-2-(2-methoxyethyl)-1H-imidazo[4,5-c]quinolin-4-amine (750 mg, 2.28 mmol) was dissolved in 30 mL of anhydrous CH₂Cl₂ and cooled to 0° C. under N₂. To the stirred solution were added Et₃N (0.64 mL, 4.56 mmol) and methanesulfonyl chloride (176 μL, 2.28 mmol) and the reaction was allowed to warm to room temperature over 2 h. The reaction mixture was then quenched by addition of saturated NaHCO₃ solution (30 mL). The organic layer was separated and washed with H₂O (3×25 mL) and brine, dried over Na₂SO₄ and concentrated under reduced pressure to give a tan foam. The foam was dissolved in a minimum amount of MeOH and Et₂O was added and a solid percipitated from the solution. The off-white solid was isolated by filtration and dried to yield 385 mg of N-(2-{2-[4-amino-2-(2-methoxyethyl)-1H-imidazo[4,5-c]quinolin-1-yl]ethoxy}ethyl)methanesulfoneamide. m.p. 114.0–117.0° C.;

MS 408 (M+H)⁺;

1H NMR (300 MHz, DMSO-d₆) δ8.05 (d, J=7.6 Hz, 1 H); 7.61 (d, J=8.5 Hz, 1 H); 7.42 (t, J=8.5 Hz, 1 H); 7.24 (t, J=7.0 Hz, 1 H); 6.99 (t, J=4.4 Hz, 1 H); 6.51 (s, 2 H);4.76 (t, J=5.0 Hz, 2 H); 3.88–3.81 (m, 4 H); 3.41 (t, J=5.4 Hz, 2 H); 3.31 (s, 3 H); 3.23 (t, J=6.9 Hz, 2 H); 3.04–2.99 (m, 2 H); 2,81 (s, 3 H);

¹³C (75 MHz, DMSO-d₆) 151.9, 145.0, 132.7, 126.7, 126.6, 121.5, 120.5, 115.1, 70.5, 70.2, 69.3, 58.5, 45.4, 42.4, 27.6.

Anal. Calcd for C₁₈H₂₅N₅O₄S·0.23 H₂O: %C, 52.52; %H, 6.23; %N, 17.01. Found: %C, 52.55; %H, 6.17; %N, 16.66

EXAMPLE 2

N-(2-{2-[4-amino-2-(2-methoxyethyl)-6,7,8,9-tetrahydro-1H-imidazo[4,5-c]quinolin-1-yl]ethoxy}ethyl)methanesulfonamide

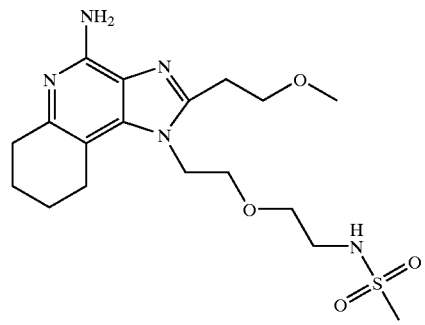

Part A

1-[2-(2-Aminoethoxy)ethyl]-2-(2-methoxyethyl)-1H-imidazo[4,5-c]quinolin-4-amine (10.0 g, 27.3 mmol) was dissolved in 50 mL of trifluoroacetic acid and treated with PtO₂ (1.0 g). The reaction mixture was shaken under H₂ (3 Kg/cm²). After 4 d, an additional 0.5 g of PtO₂ was added and hydrogenation was continued for an additional 3 d. The reaction was then filtered through Celite and concentrated under reduced pressure to give a brown oil. The oil was dissolved in 200 mL of H₂O then made basic (pH~11) by addition of 10% NaOH solution. This was then extracted with CHCl₃ (5×75 mL) and the combined organic layers were dried over Na₂SO₄ and concentrated to give 5.17 g of 1-[2-(2-aminoethoxy)ethyl]-2-(2-methoxyethyl)-6,7,8,9-tetrahydro-1H-imidazo[4,5-c]quinolin-4-amine as a tan solid.

MS 334 (M+H)⁺;

¹H NMR (300 MHz, CDCl₃) δ5.19 (s, 2 H); 4.49 (t, J=5.4 Hz, 2 H); 3.84 (t, J=6.6 Hz, 2 H); 3.71 (t, J=5.4 Hz, 2 H), 3.36 (t, J=5.2 Hz, 2 H); 3.28 (s, 3 H); 3.15 (t, J=6.6 Hz, 2 H); 2.95 (m, 2 H); 2.82 (m, 2 H); 2.76 (t, J=5.1 Hz, 2 H); 1.84 (m, 4 H), 1.47 (br s, 2 H).

Part B

1-[2-(2-Aminoethoxy)ethyl]-2-(2-methoxyethyl)-6,7,8,9-tetrahydro-1H-imidazo[4,5-c]quinolin-4-amine (1.00 g, 3.00 mmol) was dissolved in 30 mL of anhydrous $CH_2Cl_2$ and cooled to 0° C. under $N_2$. To the stirred solution were added $Et_3N$ (0.84 mL, 6.00 mmol) and methanesulfonyl chloride (232 μL, 3.00 mmol) and the reaction was allowed to warm to room temperature overnight. The reaction mixture was then quenched by addition of saturated $NaHCO_3$ solution (30 mL). The organic layer was separated and washed with $H_2O$ and brine, dried over $Na_2SO_4$ and concentrated under reduced pressure to give a yellow solid. The solid was triturated with $Et_2O$ and a few drops of MeOH. The resulting white powder was isolated by filtration and further purified by column chromatography ($SiO_2$, 3% MeOH/$CHCl_3$ saturated with aqueous $NH_4OH$) to give 389 mg of N-(2-{2-[4-amino-2-(2-methoxyethyl)-6,7,8,9-tetrahydro-1H-imidazo[4,5-c]quinolin-1-yl]ethoxy}ethyl)methanesulfonamide as a white powder. m.p. 151.0–153.0° C.;

MS 412 $(M+H)^+$;

$^1$H NMR (300 MHz, DMSO-$d_6$) δ7.00 (t, J=5.4 Hz, 1 H); 5.68 (s, 2 H); 4.44 (t, J=5.1 Hz, 2 H); 3.77 (t, J=6.8 Hz, 2 H); 3.68 (t, J=5.0 Hz, 2 H); 3.39 (t, J=5.8 Hz, 2 H); 3.28 (s, 3 H); 3.11–2.99 (m, 4 H); 2.92 (m, 2 H), 2.82 (s, 3 H); 2.65 (m, 2 H); 1.75 (m, 4 H);

$^{13}$C (75 MHz, DMSO-$d_6$) 151.3, 149.3, 146.3, 138.4, 124.9, 105.6, 70.6, 70.5, 70.1, 44.5, 42.4, 32.7, 27.6, 23.8, 23.1, 23.0.

Anal. Calcd for $C_{18}H_{29}N_5O_4S$: %C, 52.54; %H, 7.10; %N, 17.02. Found: %C, 52.47; %H, 7.22; %N, 16.83.

EXAMPLE 3

N-(2-{2-[4-amino-2-(2-methoxyethyl)-1H-imidazo[4,5-c]quinolin-1-yl]ethoxy}ethyl)-N-methylmethanesulfonamide

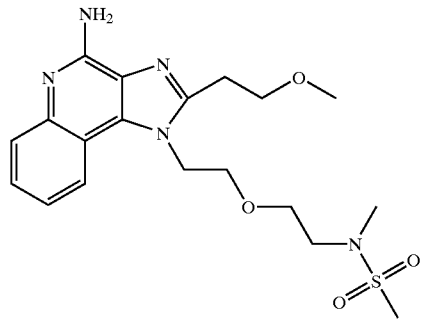

Part A

Sodium hydride (60% oil dispersion, 9.1 g, 228 mmol) was placed in a round bottom flask and washed with hexanes (3×) under $N_2$. The dried sodium hydride was treated with 800 mL of anhydrous THF. A solution of tert-butyl 2-(2-azidoethoxy)ethylcarbamate (41.9 g, 182 mmol) in 200 mL of THF was then added to the stirred sodium hydride solution over 40 min. After addition was complete, the reaction was stirred an additional 20 min followed by addition of methyl iodide (13.6 mL, 218 mmol). After stirring overnight, the reaction was quenched with 300 mL of saturated $NaHCO_3$ solution. The reaction mixture was then treated with 200 mL of $H_2O$ and 1 L of $Et_2O$. The organic phase was separated and washed with $H_2O$ and brine. The organic portion was then dried over $MgSO_4$ and concentrated under reduced pressure to give 41.9 g of tert-butyl 2-(2-azidoethoxy)ethyl(methyl)carbamate as a yellow liquid.

Part B

A solution of tert-butyl 2-(2-azidoethoxy)ethyl(methyl)carbamate (41.9 g, 170 mmol) in 600 mL of MeOH was treated with 2.5 g of 10% Pd on carbon and shaken under $H_2$ (3 Kg/cm$^2$) for 24 h. The solution was then filtered through a Celite pad and concentrated to give 37.2 g of crude tert-butyl 2-(2-aminoethoxy)ethyl(methyl)carbamate as a light yellow liquid.

Part C

A stirred solution of 4-chloro-3-nitroquinoline (32.3 g, 155 mmol) in 400 mL of anhydrous $CH_2Cl_2$, under $N_2$, was treated with triethylamine (43.1 mL, 310 mmol) and tert-butyl 2-(2-aminoethoxy)ethyl(methyl)carbamate (37.2 g, 171 mmol). After stirring overnight, the reaction mixture was washed with $H_2O$ (2×300 mL) and brine (300 mL). The organic portion was dried over $Na_2SO_4$ and concentrated to give a brown oil. Column chromatography ($SiO_2$, 33% ethyl acetate/hexanes-67% ethyl acetate/hexanes) gave 46.7 g of tert-butyl methyl(2-{2-[(3-nitroquinolin-4-yl)amino]ethoxy}ethyl)carbamate as a yellow solid.

Part D

A solution of tert-butyl methyl(2-{2-[(3-nitroquinolin-4-yl)amino]ethoxy}ethyl)carbamate (6.56 g, 16.8 mmol) in 75 mL of toluene was treated with 0.5 g of 5% Pt on carbon and shaken under $H_2$ (3 Kg/cm$^2$) for 24 h. The solution was then filtered through a Celite pad and concentrated to give 6.8 g of crude tert-butyl 2-{2-[(3-aminoquinolin-4-yl)amino]ethoxy}ethyl(methyl)carbamate as an orange syrup which was carried on without further purification.

Part E

A solution of tert-butyl 2-{2-[(3-aminoquinolin-4-yl)amino]ethoxy}ethyl(methyl)carbamate (6.05 g, 16.8 mmol) in 200 mL of anhydrous $CH_2Cl_2$ was cooled to 0° C. and treated with triethylamine (2.40 mL, 17.2 mmol). Methoxypropionyl chloride (1.72 mL, 17.2 mmol) was then added dropwise over 5 min. The reaction was then warmed to room temperature and stirring was continued for 3 h. The reaction mixture was then concentrated under reduced pressure to give an orange solid. This was dissolved in 200 mL of EtOH and 7.2 mL of triethylamine was added. The mixture was heated to reflux and stirred under $N_2$ overnight. The reaction was then concentrated to dryness under reduced pressure and treated with 300 mL of $Et_2O$. The mixture was then filtered and the filtrate was concentrated under reduced pressure to give a brown solid. This was dissolved in 300 mL of $CH_2Cl_2$ and washed with $H_2O$ and brine. The organic portion was dried over $Na_2SO_4$ and concentrated under reduced pressure to give a brown oil. The oil was dissolved in 100 mL of hot MeOH and treated with activated charcoal. The hot solution was filtered and concentrated to give 7.20 g of tert-butyl 2-{2-[2-(2-methoxyethyl)-1H-imidazo[4,5-c]quinolin-1-yl]ethoxy}ethyl(methyl)carbamate as a yellow syrup.

Part F

A solution of tert-butyl 2-{2-[2-(2-methoxyethyl)-1H-imidazo[4,5-c]quinolin-1-yl]ethoxy}ethyl(methyl)carbamate (7.20 g, 16.8 mmol) in 200 mL of $CH_2Cl_2$ was treated with MCPBA (77%, 4.32 g, 19.3 mmol). After stirring 6 h, the reaction mixture was treated with saturated $NaHCO_3$ solution and the layers were separated. The organic portion was washed with $H_2O$ and brine then dried over $Na_2SO_4$ and concentrated to give 7.05 g of tert-butyl 2-{2-[2-(2-methoxyethyl)-5-oxido-1H-imidazo[4,5-c]quinolin-1-yl]ethoxy}ethyl(methyl)carbamate as a light brown solid.

Part G

A solution of tert-butyl 2-{2-[2-(2-methoxyethyl)-5-oxido-1H-imidazo[4,5-c]quinolin-1-yl]ethoxy}ethyl (methyl)carbamate (7.05 g, 15.9 mmol) in 100 mL of 1,2-dichloroethane was heated to 80° C. and treated with 5 mL of concentrated NH$_4$OH solution. To the rapidly stirred solution was added solid p-toluenesulfonyl chloride (3.33 g, 17.5 mmol) over a 10 min period. The reaction mixture was treated with an additional 5 mL concentrated NH$_4$OH solution and then sealed in a pressure vessel and heating was continued for 4 h. The reaction mixture was then cooled and treated with 100 mL of CH$_2$Cl$_2$. The reaction mixture was then washed with H$_2$O, 1% Na$_2$CO$_3$ solution (3×) and brine. The organic portion was dried over Na$_2$SO$_4$ and concentrated to give 6.50 g of tert-butyl 2-{2-[4-amino-2-(2-methoxyethyl)-1H-imidazo[4,5-c]quinolin-1-yl]ethoxy}ethyl(methyl)carbamate as a brown oil Part H Tert-butyl 2-{2-[4-amino-2-(2-methoxyethyl)-1H-imidazo[4,5-c]quinolin-1-yl]ethoxy}ethyl(methyl)carbamate (6.50 g, 14.7 mmol) was dissolved in 100 mL of EtOH and treated with 20 mL of 2M HCl in EtOH and the mixture was heated to reflux with stirring. After 6 h, the reaction mixture was cooled and filtered to give a gummy solid. The solid was washed with EtOH and Et$_2$O and dried under vacuum to give the hydrochloride salt as a light brown powder. The free base was made by dissolving the hydrochloride salt in 50 mL of H$_2$O and treating with 5 mL of concentrated NH$_4$OH. The aqueous suspension was extracted with CHCl$_3$ (5×50 mL). The combined organic layers were dried over Na$_2$SO$_4$ and concentrated to give 3.93 g of 2-(2-methoxyethyl)-1-{2-[2-(methylamino)ethoxy]ethyl}-1H-imidazo[4,5-c]quinolin-4-amine as a tan powder. MS 344 (M+H)$^+$;

$^1$H NMR (300 MHz, DMSO-d$_6$) δ8.07 (d, J=7.7 Hz, 1 H); 7.62 (dd, J=1.0, 8.3 Hz, 1 H); 7.42 (ddd, J=1.0, 7.1, 8.2 Hz, 1 H); 7.22 (ddd, J=1.1, 7.1, 8.2 Hz, 1 H); 6.49 (s, 2 H); 4.75 (t, J=5.1 Hz, 2 H); 3.83 (t, J=6.8 Hz, 4 H); 3.35 (t, J=5.6 Hz, 2); 3.30 (s, 3 H); 3.21 (t, J=6.9 Hz, 2 H); 2.45 (t, J=5.6 Hz, 2 H); 2.12 (s, 3 H).

Part I 2-(2-Methoxyethyl)-1-{2-[2-(methylamino)ethoxy]ethyl}-1H-imidazo[4,5-c]quinolin-4-amine (1.00 g, 2.92 mmol) was dissolved in 30 mL of anhydrous CH$_2$Cl$_2$ and cooled to 0° C. under N$_2$. To the stirred solution were added Et$_3$N (0.81 mL, 5.81 mmol) and methanesulfonyl chloride (226 μL, 2.92 mmol) and the reaction was allowed to warm to room temperature overnight. The reaction mixture was then quenched by addition of saturated NaHCO$_3$ solution (30 mL) and CH$_2$Cl$_2$ (30 mL). The organic layer was separated and washed with H$_2$O and brine, dried over Na$_2$SO$_4$ and concentrated under reduced pressure. Crystallization of the residue from EtOAc and CH$_2$Cl$_2$ gave 756 mg of N-(2-{2-[4-amino-2-(2-methoxyethyl)-1H-imidazo[4,5-c]quinolin-1-yl]ethoxy}ethyl)-N-methylmethanesulfonamide as tan crystals. m.p. 145.0–146.5° C.;

MS 422 (M+H)$^+$;

$^1$H NMR (300 MHz, DMSO-d$_6$) δ8.06 (d, J=7.8 Hz, 1 H); 7.61 (dd, J=0.9, 8.3 Hz, 1 H); 7.42 (t, J=7.2 Hz, 1 H); 7.23 (ddd, J=1.0, 7.0, 8.0 Hz, 1 H); 6.50 (s, 2 H); 4.77 (t, J=5.0 Hz, 2 H); 3.87 (t, J=5.0 Hz, 2 H); 3.83 (t, J=6.8 Hz, 2 H); 3.48 (t, J=5.5 Hz, 2 H); 3.30 (s, 3 H); 3.22 (t, J=6.8 Hz, 2 H); 3.13 (t, J=5.5 Hz, 2 H); 2.77 (s, 3 H); 2.63 (s, 3 H);

$^{13}$C NMR (75 MHz, DMSO-d$_6$) δ153.9, 153.8, 147.0, 134.6, 128.6, 128.5, 123.4, 122.5, 117.0, 72.4, 71.2, 60.4, 51.1, 47.3, 37.3, 37.2, 29.6.

Anal. Calcd for C$_{19}$H$_{27}$N$_5$O$_4$S: %C, 54.14; %H, 6.46; %N, 16.61. Found: %C, 53.92; %H, 6.32; %N, 16.47.

EXAMPLE 4

N-(2-{2-[4-amino-2-(2-methoxyethyl)-6,7,8,9-tetrahydro-1H-imidazo[4,5-c]quinolin-1-yl]ethoxy}ethyl)-N-methylmethanesulfonamide

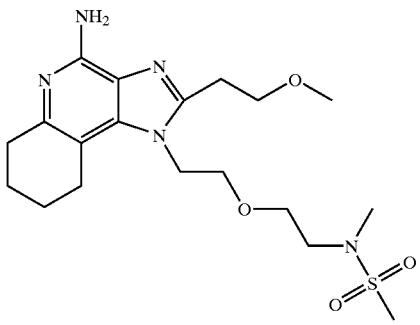

Part A 2-(2-Methoxyethyl)-1-{2-[2-(methylamino)ethoxy]ethyl}-1H-imidazo[4,5-c]quinolin-4-amine (4.22 g, 12.3 mmol) was dissolved in 25 mL of trifluoroacetic acid and treated with PtO$_2$ (0.5 g). The reaction mixture was shaken under H$_2$ (3 Kg/cm$^2$). After 4 d, an additional 0.5 g of PtO$_2$ was added and hydrogenation was continued for an additional 3 d. The reaction mixture was then filtered through Celite and concentrated under reduced pressure to give a yellow oil. The yellow oil was dissolved in 50 mL of H$_2$O and extracted with 50 mL of CHCl$_3$. The organic portion was removed and discarded. The aqueous portion was then made basic (pH~12) by addition of 10% NaOH solution. This was then extracted with CHCl$_3$ (6×50 mL) and the combined organic layers were dried over Na$_2$SO$_4$ and concentrated to a brown oil. The brown oil was dissolved in 100 mL of hot MeOH and treated with 1 g of activated charcoal. The hot solution was filtered through Celite and concentrated to dryness. The resulting gummy solid was concentrated several times with Et$_2$O to give 3.19 g of 2-(2-methoxyethyl)-1-{2-[2-(methylamino)ethoxy]ethyl}-6,7,8,9-tetrahydro-1H-imidazo[4,5-c]quinolin-4-amine as an off-white powder. MS 348 (M+H)$^+$;

$^1$H NMR (300 MHz, CDCl$_3$) δ4.84 (s, 2 H); 4.48 (t, J=5.7 Hz, 2 H); 3.84 (t, J=6.7 Hz, 2 H); 3.70 (t, J=5.7 Hz, 2 H); 3.46 (t, J=5.1 Hz, 2 H); 3.36 (s, 3 H); 3.14 (t, J=6.7 Hz, 2 H); 2.96 (m, 2 H); 2.83 (m, 2 H); 2.65 (t, J=5.1 Hz, 2 H); 2.36 (s, 3 H); 1.85 (m, 4 H).

Part B (2-(2-Methoxyethyl)-1-{2-[2-(methylamino)ethoxy]ethyl}-6,7,8,9-tetrahydro-1H-imidazo[4,5-c]quinolin-4-amine (750 mg, 2.16 mmol) was dissolved in 30 mL of anhydrous CH$_2$Cl$_2$ and cooled to 0° C. under N$_2$. To the stirred solution were added Et$_3$N (0.60 mL, 4.32 mmol) and methanesulfonyl chloride (167 μL, 2.16 mmol) and the reaction was allowed to warm to room temperature over 3 h. The reaction mixture was then quenched by addition of saturated NaHCO$_3$ solution (30 mL) and CH$_2$Cl$_2$ (30 mL). The organic layer was separated and washed with H$_2$O and brine, dried over Na$_2$SO$_4$ and concentrated under reduced pressure. Purification by column chromatography (SiO$_2$, 3–5% MeOH/CHCl$_3$ saturated with aqueous NH$_4$OH) gave the product as a colorless glass. The material was then concentrated with iso-propyl alcohol to give a syrup which solidified upon standing in the freezer. The solid was dried under vacuum to give 437 mg of N-(2-{2-[4-amino-2-(2-methoxyethyl)-6,7,8,9-tetrahydro-1H-imidazo[4,5-c]quinolin-1-yl]ethoxy}ethyl)-N-methylmethanesulfonamide as off-white crystals.

m.p. 115.3–117.8° C.;
MS 426 (M+H)$^+$;
$^1$H NMR (300 MHz, DMSO-d$_6$) δ5.65 (s, 2 H); 4.44 (t, J=5.2 Hz, 2 H); 3.76 (t, J=6.9 Hz, 2 H), 3.70 (t, J=5.3 Hz, 2 H); 3.47 (t, J=5.5 Hz, 2 H); 3.27 (s, 3 H); 3.15 (t, J=5.5 Hz, 2 H); 3.08 (t, J=6.9 Hz, 2 H); 2.93 (m, 2 H) ; 2.78 (s, 3 H); 2.65 (s, 3 H); 2.64 (m, 2 H); 1.74 (m, 4 H);
$^{13}$C NMR (75 MHz, DMSO-d$_6$) δ151.2, 149.3, 146.3, 138.5, 124.9, 105.6, 70.6, 70.5, 69.2, 58.4, 49.2, 44.5, 35.4, 35.2, 32.7, 27.6, 23.8, 23.1, 23.0.
Anal. Calcd for C$_{19}$H$_{27}$N$_5$O$_4$S.0.40 C$_3$H$_8$O: %C, 53.97; %H, 7.67; %N, 15.58. Found: %C, 53.71; %H, 7.48; %N, 15.77.

EXAMPLE 5

2-Butyl-1-{2-[2-(1,1-dioxidoisothiazolidin-2-yl) ethoxy]ethyl}-1H-imidazo[4,5-c]quinolin-4-amine.

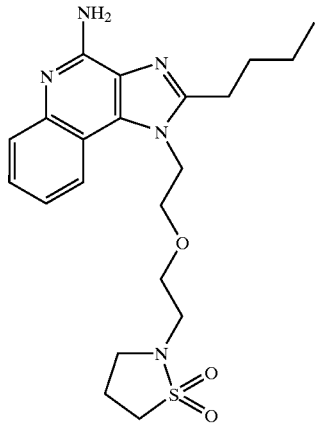

Under a nitrogen atmosphere, chloropropylsulfonyl chloride (0.05 ml, 0.46 mmol) was added dropwise to a solution of 1-[2-(2-aminoethoxy)ethyl]-2-butyl-1H-imidazo[4,5-c] quinolin-4-amine (0.12 g, 0.37 mmol) and triethylamine (0.065 ml, 0.46 mmol) in dichloromethane (5 ml). The reaction was stirred for 20 hours followed by removal of the solvent in vacuo. The resulting off-white solid was dissolved in N,N-dimethylformamide (5 mL) and 1,8-diazabicyclo [5.4.0]undec-7-ene (0.087 ml, 0.58 mmol) was added. The reaction was stirred for 18 hours under an atmosphere of nitrogen and then quenched with water and extracted with dichloromethane (2×). The organic fractions were combined, washed with water followed by brine, dried (Na$_2$SO$_4$), filtered, and concentrated in vacuo to provide an off-white solid. Recrystallization from ethyl acetate yielded 0.068 g of 2-butyl-1-{2-[2-(1,1-dioxidoisothiazolidin-2-yl) ethoxy]ethyl}-1H-imidazo[4,5-c]quinolin-4-amine as off-white crystals, m.p. 152–154° C.
$^1$H-NMR (300 MHz, DMSO-d$_6$): δ8.06 (d, J=8.1Hz, 1 H), 7.62 (d, J=7.9 Hz, 1H), 7.42 (t, J=7.6 Hz, 1H), 7.23 (t, J=7.5 Hz, 1H), 6.52 (s, 2H), 4.73 (t, J=4.99 Hz, 2H), 3.86 (t, J=5.0 Hz, 2H), 3.46 (t, J=5.3 Hz, 2H), 3.07 (t, J=7.66 Hz, 2H), 2.97–2.87 (m, 6H), 2.04 (quintet, J=6.8 Hz, 2H), 1.81 (quintet, J=7.6 Hz, 2H), 1.46 (sextet, J=7.4 Hz, 2H), 0.96 (t, J=7.3 Hz, 3H);
$^{13}$C-NMR (75 MHz, DMSO-d$_6$): δ154.6, 152.9, 145.1, 133.0, 126.8, 126.6, 121.6, 120.8, 115.3, 69.2, 69.1, 47.0, 45.5, 45.0, 43.7, 29.3, 26.2, 21.9, 18.1, 13.7;
Anal calcd for C$_{21}$H$_{29}$N$_5$O$_3$S*0.25H$_2$O: %C, 57.84; %H, 6.82; %N, 16.06; %S, 7.35.
Found: %C, 57.90; %H, 6.79; %N, 15.92; %S, 7.55.

EXAMPLES 6–26

Part A
A solution of tert-butyl 2-{2-[(3-aminoquinolin-4-yl) amino]ethoxy}ethylcarbamate (3.46 g, 10.0 mmol) in 50 mL of toluene was treated with triethylorthovalerate (2.5 mL, 14.5 mmol) and the reaction mixture was heated to reflux. A 25 mg portion of pyridinium hydrochloride was then added and refluxing was continued for 4 h. The reaction was then concentrated to dryness under reduced pressure. The residue was dissolved in 50 mL of CH$_2$Cl$_2$ and washed with saturated NaHCO$_3$, H$_2$O and brine. The organic portion was dried over Na$_2$SO$_4$ and concetrated to give a green oil. The green oil was dissolved in 50 mL of hot MeOH and treated with activated charcoal. The hot solution was filtered and concentrated to give 4.12 g of tert-butyl 2-[2-(2-butyl-1H-imidazo[4,5-c]quinolin-1-yl)ethoxy]ethylcarbamate as a yellow oil.
Part B
A solution of tert-butyl 2-[2-(2-butyl-1H-imidazo[4,5-c] quinolin-1-yl)ethoxy]ethylcarbamate (4.12 g, 10.0 mmol) in 50 mL of CH$_2$Cl$_2$ was treated with 3-chloroperoxybenzoic acid (MCPBA, 77%, 2.5 g, 11.2 mmol). After stirring for 5 h, the reaction mixture was treated with saturated NaHCO$_3$ solution and the layers were separated. The organic portion was washed with H$_2$O and brine then dried over Na$_2$SO$_4$ and concentrated to give 3.68 g of tert-butyl 2-[2-(2-butyl-5-oxido-1H-imidazo[4,5-c]quinolin-1-yl)ethoxy] ethylcarbamate as a light brown foam.
Part C
A solution of tert-butyl 2-[2-(2-butyl-5-oxido-1H-imidazo[4,5-c]quinolin-1-yl)ethoxy]ethylcarbamate (3.68 g, 8.60 mmol) in 100 mL of 1,2-dichloroethane was heated to 80° C. and treated with 10 mL of concentrated NH$_4$OH solution. To the rapidly stirred solution was added solid p-toluenesulfonyl chloride (1.87 g, 9.81 mmol) over a 10 min period. The reaction mixture was then sealed in a pressure vessel and heating was continued for 2 h. The reaction mixture was then cooled and treated with 100 mL of CH$_2$Cl$_2$. The reaction mixture was then washed with H$_2$O, 1% Na$_2$CO$_3$ solution (3×) and brine. The organic portion was dried over Na$_2$SO$_4$ and concentrated to give 3.68 g of tert-butyl 2-[2-(4-amino-2-butyl-1H-imidazo[4,5-c] quinolin-1-yl)ethoxy]ethylcarbamate as a light brown foam.
Part D
Tert-butyl 2-[2-(4-amino-2-butyl-1H-imidazo[4,5-c] quinolin-1-yl)ethoxy]ethylcarbamate (3.68 g, 8.60 mmol) was suspended in 20 mL of 2M HCl in EtOH and the mixture was heated to reflux with stirring. After 3 h, the reaction mixture was concentrated to give a solid. The solid was triturated with hot EtOH (50 mL) and filtered to give 2.90 g of the product as the hydrochloride salt. The free base was made by dissolving the hydrochloride salt in 50 mL of H$_2$O and treating with 5 mL of concentrated NH$_4$OH. The aqueous suspension was extracted with CH$_2$Cl$_2$ (3×50 mL). The combined organic layers were dried over Na$_2$SO$_4$ and concentrated to give 1-[2-(2-aminoethoxy)ethyl]-2-butyl-1H-imidazo[4,5-c]quinolin-4-amine as a tan powder.
MS 328 (M+H)$^+$;
$^1$H NMR (300 MHz, CDCl$_3$) δ7.95 (d, J=8.3 Hz, 1 H); 7.83 (d, J=8.4 Hz, 1 H); 7.50 (m, 1H); 7.30 (m, 1 H); 5.41 (s, 2 H); 4.69 (t, J=5.6 Hz, 2 H); 3.93 (t, J=5.6 Hz, 2 H); 3.39 (t, J=5.1 Hz, 2 H); 2.97 (t, J=7.9 Hz, 2 H); 2.76 (t, J=5.1 Hz, 2 H); 1.89 (m, 2 H); 1.52 (m, 2 H); 1.26 (br s, 2 H); 1.01 (t, J=7.3 Hz, 3 H).
Part E
The compounds in the table below were prepared according to the synthetic method of step (7) of Reaction Scheme II above using the following general method.

The sulfonyl chloride or the sulfamoyl chloride (1.1 eq.) was added to a test tube containing a solution of 1-[2-(2-aminoethoxy)ethyl]-2-butyl-1H-imidazo[4,5-c]quinolin-4-amine (25 mg) in dichloromethane (5 mL). The test tube was capped and then placed on a shaker at ambient temperature for 18–20 hr. The solvent was removed by vacuum centrifugation. The residue was purified by semi-preparative HPLC using the method described above. The products were verified by accurate mass and $^1$H NMR. The table below shows the structure of the free base and the observed accurate mass (M+H).

| Example Number | Structure of Free Base | Accurate Mass (obs.) |
|---|---|---|
| 6 | 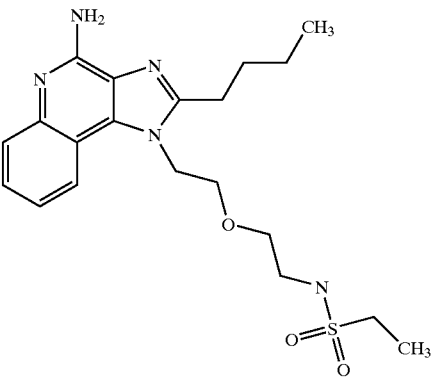 | 420.2077 |
| 7 | 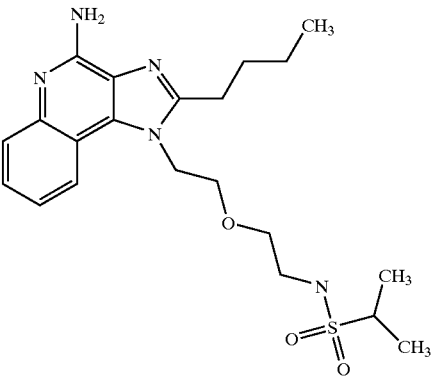 | 434.2234 |
| 8 | 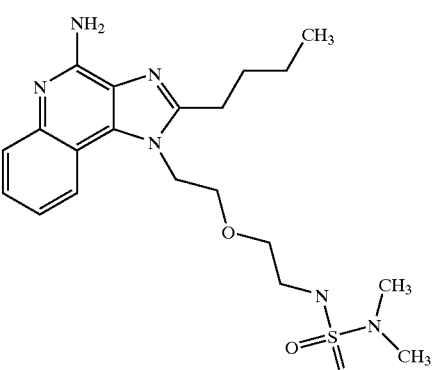 | 435.2196 |

-continued

| Example Number | Structure of Free Base | Accurate Mass (obs.) |
|---|---|---|
| 9 | | 448.2387 |
| 10 | | 468.2075 |
| 11 | | 474.1625 |

-continued

| Example Number | Structure of Free Base | Accurate Mass (obs.) |
|---|---|---|
| 12 | | 482.2214 |
| 13 | | 486.1967 |
| 14 | | 493.2009 |

-continued

| Example Number | Structure of Free Base | Accurate Mass (obs.) |
|---|---|---|
| 15 | | 493.2025 |
| 16 | | 498.2195 |
| 17 | | 504.1861 |

-continued

| Example Number | Structure of Free Base | Accurate Mass (obs.) |
|---|---|---|
| 18 | | 518.2210 |
| 19 | | 518.2243 |
| 20 | | 519.2158 |

-continued
| Example Number | Structure of Free Base | Accurate Mass (obs.) |
|---|---|---|
| 21 | 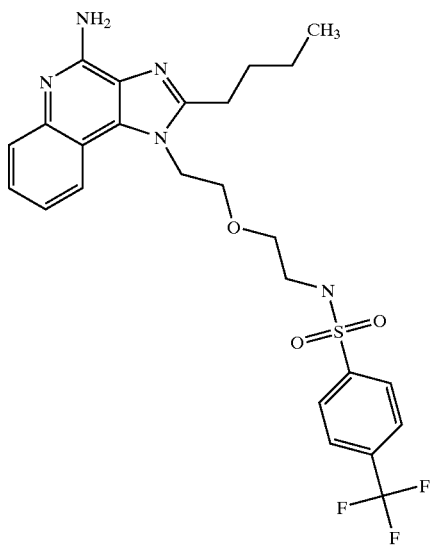 | 536.1917 |
| 22 | 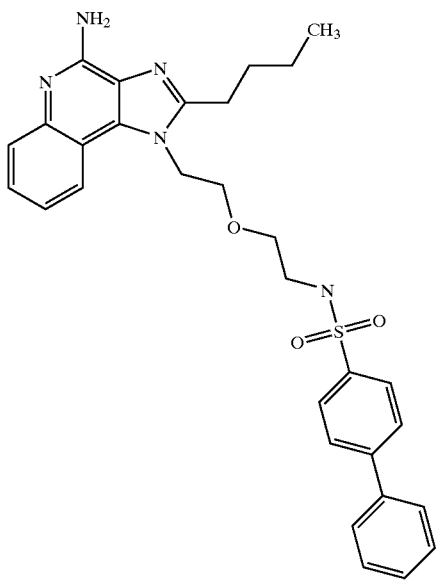 | 544.2384 |

-continued
| Example Number | Structure of Free Base | Accurate Mass (obs.) |
|---|---|---|
| 23 | 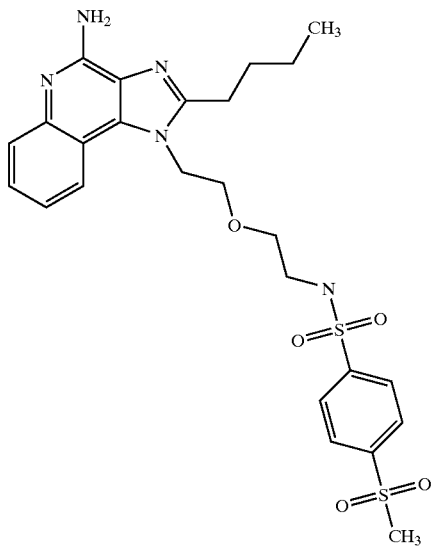 | 546.1852 |
| 24 | 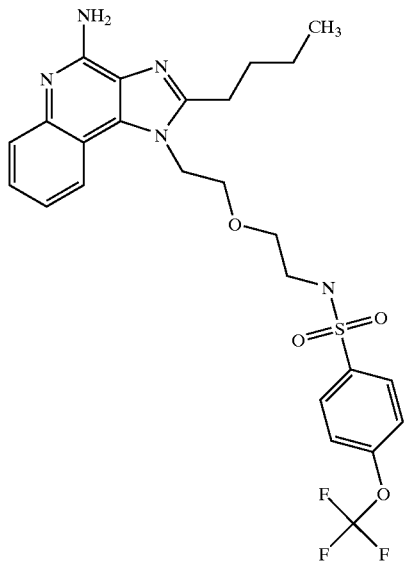 | 552.1874 |

| Example Number | Structure of Free Base | Accurate Mass (obs.) |
|---|---|---|
| 25 | | 615.2848 |
| 26 | (Chiral) | 542.2779 |

EXAMPLES 27–39

Part A

Using the general method of Part A of Examples 6–26, 4-piperidineethanol (10 g, 77.4 mmol) was reacted with di-tert-butyl dicarbonate (17.7 g, 81.3 mmol) to provide 13.1 g of tert-butyl 4-(2-hydroxyethyl)piperidine-1-carboxylate as a clear oil.

Part B

Iodine (7.97 g) was added in three portions to a solution of imidazole (3.89 g, 57.1 mmol) and triphenylphosphine (14.98 g, 57.1 mmol) in dichloromethane (350 mL). After 5 minutes a solution of the material from Part A in dichloromethane (70 mL) was added. The reaction mixture was stirred at ambient temperature overnight. More iodine (7.97 g) was added and the reaction was stirred at ambient temperature for 1 hr. The reaction mixture was washed with saturated sodium thiosulfate (2×) and brine, dried over sodium sulfate, filtered and then concentrated under reduced pressure to provide an oily residue. The residue was purified by column chromatography (silica gel eluting with 20% ethyl acetate in hexanes) to provide 15.52 g of tert-butyl 4-(2-iodoethyl)piperidine-1-carboxylate as a pale yellow oil.

Part C

Under a nitrogen atmosphere, 2-(1H-imidazo[4,5-c]quinolin-1-yl)butan-1-ol (6.5 g, 26.9 mmol) was added in three portions to a suspension of sodium hydride (1.4 g of 60%, 35.0 mmol) in anhydrous N,N-dimethylformamide. The reaction mixture was allowed to stir for 45 minutes by which time gas evolution had ceased. Tert-butyl 4-(2-iodoethyl)piperidine-1-carboxylate (10.05 g, 29.6 mmol)

was added dropwise over a period of 15 minutes. The reaction mixture was allowed to stir at ambient temperature for 2.5 hrs; then it was heated to 100° C. and stirred overnight. Analysis by HPLC showed that the reaction was about 35% complete. Saturated ammonium chloride solution was added, the resulting mixture was allowed to stir for 20 minutes and then it was extracted with ethyl acetate (2×). The ethyl acetate extracts were washed with water (2×) and then with brine, combined, dried over sodium sulfate, filtered and then concentrated under reduced pressure to provide a brown oil. The oil was purified by column chromatography (silica gel eluting sequentially with 30% ethyl acetate in hexanes, 50% ethyl acetate in hexanes, and ethyl acetate) to provide 2.2 g of tert-butyl 4-{2-[2-(1H-imidazo[4,5-c]quinolin-1-yl)butoxy]ethyl}piperidine-1-carboxylate.

Part D

Using the general method of Examples 6–26 Part H, the material from Part C was oxidized to provide tert-butyl 4-{2-[2-(5-oxido-1H-imidazo[4,5-c]quinolin-1-yl)butoxy] ethyl}piperidine-1-carboxylate as an oil.

Part E

Ammonium hydroxide solution (20 mL) was added to a solution of the material from Part D in dichloromethane (20 mL). A solution of tosyl chloride (0.99 g, 5.2 mmol) in dichloromethane (10 mL) was added over a period of 5 minutes. The resulting biphasic reaction mixture was allowed to stir overnight. The reaction mixture was diluted with chloroform and saturated sodium bicarbonate solution. The layers were separated. The organic layer was dried over sodium sulfate, filtered and then concentrated under reduced pressure to provide a brown glass. This material was purified by column chromatography (silica gel eluting first with 50% ethyl acetate in hexanes and then with ethyl acetate) to provide 1.0 g of tert-butyl 4-{2-[2-(4-amino-1H-imidazo[4,5-c]quinolin-1-yl)butoxy]ethyl}piperidine-1-carboxylate as pale yellow glassy foam.

Part F

Under a nitrogen atmosphere, tert-butyl 4-{2-[2-(4-amino-1H-imidazo[4,5-c]quinolin-1-yl)butoxy] ethyl}piperidine-1-carboxylate (1.00 g, 2.1 mmol) and 2N ethanolic hydrochloric acid (10 ml, 20 mmol) were combined and the solution was stirred at ambient temperature for 14 hours. The solvent was removed in vacuo and the resulting tan solid was dissolved in water. Saturated aqueous sodium carbonate was added until the pH reached 10. After extraction with dichloromethane (3×), the organic fractions were combined, washed with brine, dried ($Na_2SO_4$), filtered, and the majority of the solvent was removed in vacuo. Hexane was added to form a precipitate. Vacuum filtration yielded 0.5 g of 1-{1-[(2-piperidin-4-ylethoxy)methyl] propyl}-1H-imidazo[4,5-c]quinolin-4-amine as a tan powder.

$^1$H-NMR (300 MHz, DMSO-$d_6$): δ8.34 (bs, 1H), 8.19 (d, J=8.49, 1H), 7.61 (dd, J=8.31, 1.13, 1H), 7.45–7.39 (m, 1H), 7.25–7.19 (m, 1H), 6.55 (s, 2H), 5.25–5.15 (m, 1H), 4.00–3.80 (m, 2H), 3.5–3.3 (m, 2H), 2.8–2.64 (m, 2H), 2.22–2.11 (m, 2H), 2.09–1.99 (m, 2H), 1.8–1.63 (bs, 1H), 1.37–1.0 (m, 5H), 0.95–0.7 (m, 5H);

$^{13}$C-NMR (75 MHz, DMSO-$d_6$): δ152.8, 145.8, 140.6, 133.0, 127.8, 127.0, 126.9, 121.3, 121.0, 115.5, 71.8, 68.1, 58.4, 46.1, 36.3, 33.1, 32.7, 24.5, 9.9;

MS (CI) m/e 368.2459 (368.2450 calcd for $C_{21}H_{30}N_5O$).

Part G

The compounds in the table below were prepared according to the synthetic method of step (7) of Reaction Scheme II above using the following general method.

The sulfonyl chloride or the sulfamoyl chloride (1.1 eq.) was added to a test tube containing a solution of 1-{1-[(2-piperidin-4-ylethoxy)methyl]propyl}-1H-imidazo[4,5-c] quinolin-4-amine (25 mg) in dichloromethane (5 mL). The test tube was capped and then placed on a shaker at ambient temperature for 20 hr. The solvent was removed by vacuum centrifugation. The residue was purified by semi-preparative HPLC using the method described above. The products were verified by accurate mass and $^1$H NMR. The table below shows the structure of the free base and the observed accurate mass (M+H).

| Example Number | Structure of Free Base | Accurate Mass (obs.) |
|---|---|---|
| 27 | [structure] | 474.2531 |

-continued

| Example Number | Structure of Free Base | Accurate Mass (obs.) |
|---|---|---|
| 28 | | 475.2483 |
| 29 | | 488.2647 |
| 30 | | 508.2349 |
| 31 | | 514.1924 |

| Example Number | Structure of Free Base | Accurate Mass (obs.) |
|---|---|---|
| 32 | | 526.2241 |
| 33 | | 533.2315 |
| 34 | | 538.2477 |

-continued

| Example Number | Structure of Free Base | Accurate Mass (obs.) |
|---|---|---|
| 35 | | 544.2166 |
| 36 | | 559.2493 |
| 37 | | 586.2166(1) |

| Example Number | Structure of Free Base | Accurate Mass (obs.) |
| --- | --- | --- |
| 38 | | 592.2144 |
| 39 | | 655.3173 |

EXAMPLES 40–49

Part A

A solution of tert-butyl 2-{2-[(3-aminoquinolin-4-yl)amino]ethoxy}ethylcarbamate (6.92 g, 20.0 mmol) in 100 mL of toluene was treated with triethylorthoformate (4.65 mL, 28.0 mmol) and the reaction mixture was heated to reflux. A 100 mg portion of pyridinium hydrochloride was then added and refluxing was continued for 2 h. The reaction was then concentrated to dryness under reduced pressure. The residue was dissolved in 200 mL of $CH_2Cl_2$ and washed with saturated $NaHCO_3$, $H_2O$ and brine. The organic portion was dried over $Na_2SO_4$ and concentrated to give a green oil. The green oil was dissolved in 200 mL of hot MeOH and treated with 10 g of activated charcoal. The hot solution was filtered and concentrated to give 5.25 g of tert-butyl 2-[2-(1H-imidazo[4,5-c]quinolin-1-yl)ethoxy]ethylcarbamate as a light yellow syrup.

Part B

A solution of tert-butyl 2-[2-(1H-imidazo[4,5-c]quinolin-1-yl)ethoxy]ethylcarbamate (5.25 g, 14.7 mmol) in 200 mL of $CH_2Cl_2$ was treated with MCPBA (77%, 3.63 g, 16.3 mmol). After stirring overnight, the reaction mixture was treated with saturated $NaHCO_3$ solution and the layers were separated. The organic portion was washed with $H_2O$ and brine then dried over $Na_2SO_4$ and concentrated to give 4.60 g of tert-butyl 2-[2-(5-oxido-1H-imidazo[4,5-c]quinolin-1-yl)ethoxy]ethylcarbamate as a light brown foam.

Part C

A solution of tert-butyl 2-[2-(5-oxido-1H-imidazo[4,5-c]quinolin-1-yl)ethoxy]ethylcarbamate (4.60 g, 12.4 mmol) in 150 mL of 1,2-dichloroethane was heated to 80° C. and treated with 10 mL of concentrated $NH_4OH$ solution. To the rapidly stirred solution was added solid p-toluenesulfonyl chloride (2.71 g, 14.2 mmol) over a 10 min period. The reaction mixture was treated with an additional 2 mL of concentrated $NH_4OH$ solution and then sealed in a pressure vessel and heating was continued for 3 h. The reaction mixture was then cooled and treated with 100 mL of $CH_2Cl_2$. The reaction mixture was then washed with $H_2O$, 1% $Na_2CO_3$ solution (3×) and brine. The organic portion was dried over $Na_2SO_4$ and concentrated to give 4.56 g of tert-butyl 2-[2-(4-amino-1H-imidazo[4,5-c]quinolin-1-yl)ethoxy]ethylcarbamate as a light brown foam.

Part D

Tert-butyl 2-[2-(4-amino-1H-imidazo[4,5-c]quinolin-1-yl)ethoxy]ethylcarbamate (4.56 g, 12.3 mmol) was dissolved in 100 mL of EtOH and treated with 30 mL of 2M HCl in EtOH and the mixture was heated to reflux with stirring. After 3 h, the reaction mixture was concentrated to give a solid. The solid was triturated with hot EtOH (100 mL) and filtered to give the product as the hydrochloride salt. The free base was made by dissolving the hydrochloride salt in 50 mL of $H_2O$ and treating with 5 mL of concentrated $NH_4OH$. The aqueous suspension was extracted with $CH_2Cl_2$ (5×50 mL). The combined organic layers were dried over $Na_2SO_4$ and concentrated to give 1.35 g of 1-[2-(2-aminoethoxy)ethyl]-1H-imidazo[4,5-c]quinolin-4-amine as a tan powder.

MS 272 (M+H)+;
¹H NMR (300 MHz, CDCl₃) δ7.98 (d, J=8.2 Hz, 1 H); 7.88 (s, 1 H); 7.84 (d, J=8.4 Hz, 1 H); 7.54 (m, 1 H); 7.32 (m, 1 H); 5.43 (s, 2 H); 4.74 (t, J=5.2 Hz, 2 H); 3.97 (t, J=5.2 Hz, 2 H); 3.42 (t, J=5.1 Hz, 2 H); 2.78 (t, J=5.1 Hz, 2 H); 1.10 (br s, 2 H).

Part E

The compounds in the table below were prepared according to the synthetic method of step (7) of Reaction Scheme II above using the following general method.

1-[2-(2-Aminoethoxy)ethyl]-1H-imidazo[4,5-c]quinolin-4-amine (20 mg) and 1-methyl-2-pyrrolidinone (5 mL) were combined in a test tube and then heated and sonicated to provide a solution. The sulfonyl chloride (1.1 eq.) was then added to the test tube. The test tube was capped and then placed on a shaker at ambient temperature for 20 hr. The solvent was removed by vacuum centrifugation. The residue was purified by semi-preparative HPLC using the method described above. The products were verified by accurate mass and ¹H NMR. The table below shows the structure of the free base and the observed accurate mass (M+H).

| Example Number | Structure of Free Base | Accurate Mass (obs.) |
|---|---|---|
| 40 | 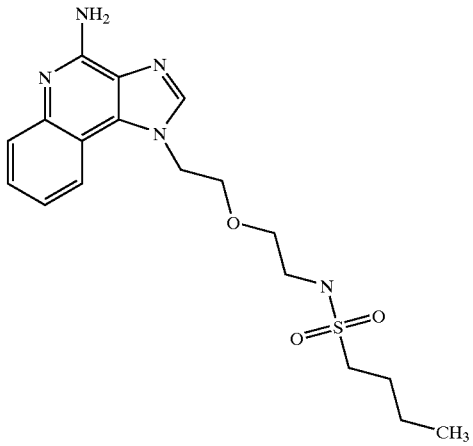 | 392.1781 |
| 41 | 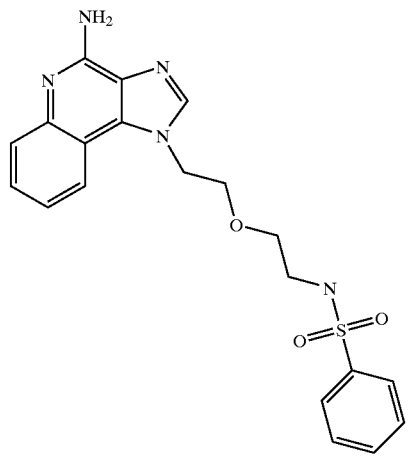 | 412.1468 |

-continued
| Example Number | Structure of Free Base | Accurate Mass (obs.) |
|---|---|---|
| 42 | 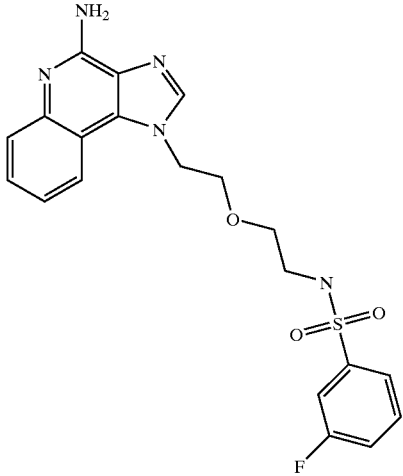 | 430.1348 |
| 43 | 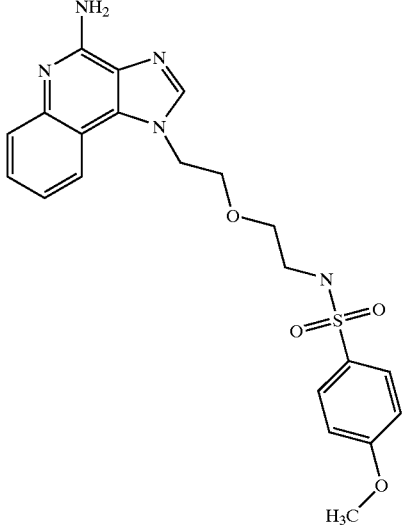 | 442.1572 |
| 44 | 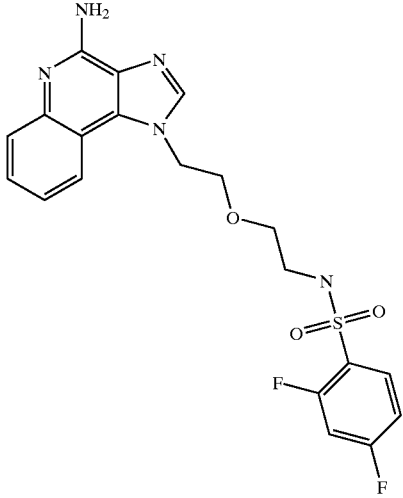 | 448.1259 |

-continued
| Example Number | Structure of Free Base | Accurate Mass (obs.) |
| --- | --- | --- |
| 45 | 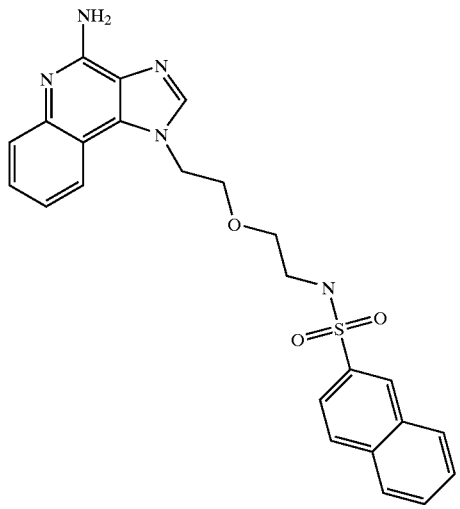 | 462.1571 |
| 46 | 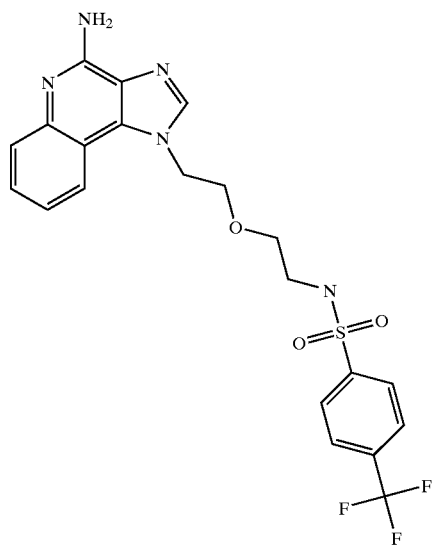 | 480.1274 |

-continued
| Example Number | Structure of Free Base | Accurate Mass (obs.) |
|---|---|---|
| 47 | 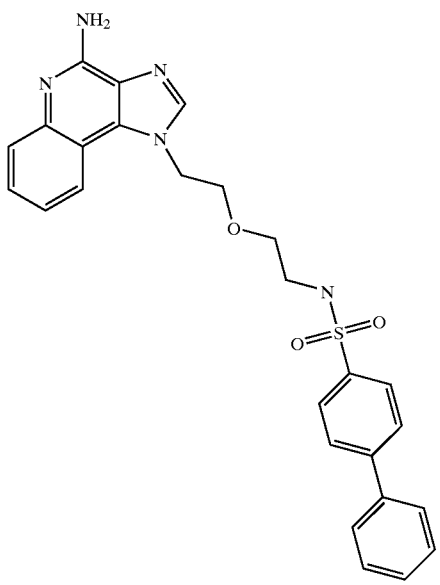 | 488.1722 |
| 48 | 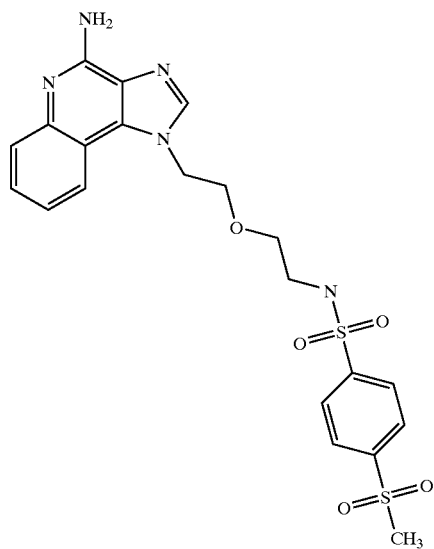 | 490.1224 |

| Example Number | Structure of Free Base | Accurate Mass (obs.) |
|---|---|---|
| 49 | 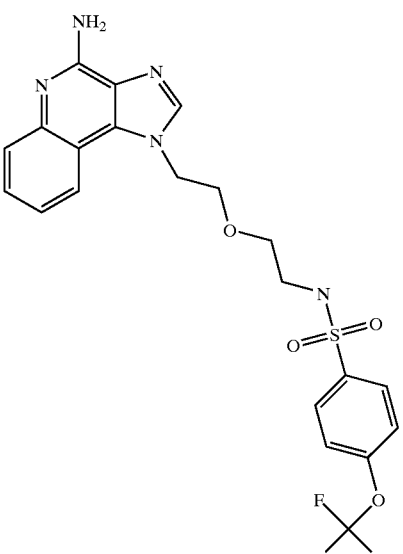 | 496.1230 |

EXAMPLE 50

N-[10-(4-amino-2-methyl-1H-imidazo[4,5-c]quinolin-1-yl)-4,7-dioxadecyl]-5-dimethylaminonaphthalene-1-sulfonamide

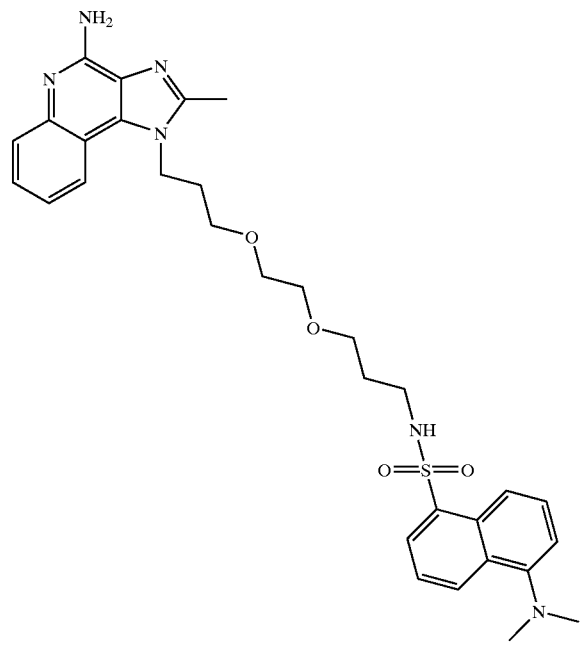

Part A 4,7-Dioxadecane-1,10-diamine (32.6 g, 0.185 mole) in acetonitrile (100 mL) was chilled in an ice bath. To this was slowly added dropwise dansyl chloride (5 g, 0.0185 mole) dissolved in acetonitrile (60 mL) over a 20 min. period. Stirring in an ice bath was continued for 1.5 hr. The reaction mixture was poured into water (about 300 mL) and extracted with dichloromethane (2×100 mL). The combined extracts were washed with water and dried to give an oil. The oil was purified by column chromatography (silica gel eluting with acetonitrile containing increasing amounts of ethanol) to provide 4.6 g of N-(10-amino-4,7-dioxadecyl)-5-dimethylaminonaphthalene-1-sulfonamide as a viscous oil.

$^1$H-NMR (500 MHz, CDCl$_3$) 1.65 (2H, quin), 1.75 (2H, quin), 2.80 (2H, t, 6.59 Hz), 2.87 (6H, s), 3.03 (2H, t, 6.1 Hz), 3.43 (2H, m), 3.47 (2H, m), 3.52 (2H, m), 3.59 (2H, t, 6.22 Hz), 7.18 (1H, d, J=7.08 Hz)), 7.56–7.49 (overlapping multiplets, 2H), 8.24 (dd, 1H, J=1.2, 7.3 Hz), 8.31 (d, 1H), 8.53 (d, 1H).

Part B

A solution of 2,4-dichloro-3-nitroquinoline (2.71 g, 0.0115 mole) in toluene (100 mL) was cooled to 0–5° C. in an ice bath. Triethylamine (1.5 g) was added in one portion. A solution of N-(10-amino-4,7-dioxadecyl)-5-dimethylaminonaphthalene-1-sulfonamide (4.6 g, 0.01159 mole) in toluene (60 mL) was added dropwise while maintaining the temperature below 10° C. The reaction was stirred at 2–5° C. for 4 hrs and at a room temperature of 21° C. overnight (18 hours). Thin layer chromatography (dichloromethane: ethanol) showed a trace of the amine starting material, but was mostly a bright yellow spot at the solvent front assumed to be the addition product. The toluene was removed by rotary evaporation to provide a viscous oil. The oil was purified by column chromatography (silica gel, dichloromethane/ethanol) to provide 2.4 g of N-[10-(2-chloro-3-nitro-4-quinolinyl)amino-4,7-dioxadecyl]-5-dimethylaminonaphthalene-1-sulfonamide.

$^1$H-NMR (CDCl$_3$) 1.62 (2H, quin), 2.05 (2H, quin), 2.87 (6H, s), 3.03 (2H, m), 3.47 (4H, m), 3.55 (2H, m), 3.65 (2H, m), 3.73 (2H, t, 5.37 Hz), 5.75 (1H, t, 4.39 Hz,NH), 6.91 (1H, t, 4.76 Hz, NH), 7.15 (1H, d, 7.32 Hz), 7.30 (1H, m), 7.50 (2H, overlapping t), 7.62 (1H, m), 7.82 (1H, d, 7.44 Hz), 7.88 (1H, d, 8.54 Hz), 8.22 (1H, m), 8.29 (1H,d, 8.42), 8.52 (1H, d, 8.06 Hz).

Part C

Material from Part B (2.2 g, 0.00357 mole) was dissolved in ethanol (150 mL). Catalyst (about 1 g of 5% Pt/C) was added and the mixture was hydrogenated using a Parr apparatus for 30 minutes. Thin layer chromatography (ethyl acetate: hexane 1:1) showed that the reaction was complete. The reaction mixture was filtered to remove the catalyst and the filtrate was evaporated to provide a sticky solid which was shown by NMR to be crude N-[10-(3-amino-2-chloro-4-quinolinyl)amino-4,7-dioxadecyl]-5-dimethylaminonaphthalene-1-sulfonamide. It was used without further purification.

¹H-NMR (500 MHz, CDCl₃) 1.60 (2H, quin), 1.90 (2H, quin), 2.87 (6H, s, NMe₂), 3.00 (2H, br s), 3.45 (4H, m), 3.53 (2H, m), 3.62 (2H, t, 5.62 Hz), 3.71 (4.30 (2H, br s, NH₂), 5.85 (1H, br s, NH), 7.11 (1H, d, J=7.32 Hz), 7.35 (1H, m), 7.44–7.48 (3H, m), 7.82 (1H, d), 8.18 (1H, dd, J=1.1, 7.2 Hz), 8.30 (1H, d, 8.66 Hz), 8.49 (1H, d, 8.54 Hz).

¹³C-NMR (125 MHz) 28.48 (CH₂), 30.08 (CH₂), 41.93 (CH₂), 45.27 (CH₃), 45.28(CH₂), 69.75 (CH₂), 69.83 (CH₂), 70.08 (CH₂), 70.38 (CH₂), 114.99 (CH), 118.84 (CH), 120.84 (CH), 123.02 (CH), 123.50 (C), 125.67 (CH), 126.22 (CH), 128.01 (CH), 128.57 (C) 128.67 (CH), 129.22 (CH), 129.52 (C ), 129.74 (C ), 130.09 (CH), 134.72 (C), 137.17 (C), 141.82 (C), 142.03 (C), 151.75 (C).

Part D

A portion (1 g, 1.708 mmol) of the material from Part C was dissolved in tetrahydrofuran (30 mL) and then cooled in an ice-bath to about 5° C. Freshly distilled acetyl chloride (0.13 g, 1.78 mmol) was added with stirring. The yellow solid which immediately precipitated was isolated by filtration and washed with tetrahydrofuran. Standing in air gave an oily solid (possibly hygroscopic). FAB (fast atom bombardment) mass spectrum suggested that this was the desired N-[10-(3-acetamido-2-chloro-4-quinolinyl)amino-4,7-dioxadecyl]-5-dimethylaminonaphthalene-1-sulfonamide hydrochloride together with an undetermined amount of starting material. This solid was carried on to Part E without additional purification.

Part E

The crude salt from Part D was dissolved in dry methanol containing 7% ammonia (20 mL). The solution was heated at 150° C. in a bomb for 6½ hrs. The reaction mixture was cooled and then concentrated. The residue was combined with acetone. Undissolved material was removed by filtration. The filtrate was concentrated and the residue was purified by column chromatography (silica gel; ethanol/dichloromethane) to provide 0.45 g of a brown oil.

¹H-NMR (400 MHz, CDCl₃) 1.53 (2H, t, 7.08 Hz), 2.05 (2H, m), 2.45 (3H, s), 2.70 (6H, s), 2.90 (2H, t, 5.98 Hz), 3.30 (8H, br, m), 4.40 (2H, t, 6.59 Hz), 5.75 (2H, br s NH₂), 6.65 (1H, br s NHSO₂),7.00 (1H, d, 7.54 Hz), 7.14 (1H, t, 8.06 Hz), 7.30 (3H, m), 7.64 (1H, d, 8.30 Hz), 7.88 (1H, d, 8.18 Hz), 8.06 (1H, d, 7.33 Hz), 8.24 (1H, d, 8.54 Hz), 8.36 (1H, d, 8.55 Hz).

This material was then purified by high performance liquid chromatography using a Bondapak C18 12.5 nm reverse phase column (available from Waters, Milford, Mass.) eluting with a composite gradient of acetonitrile in water to provide the desired product.

EXAMPLE 51

1-[2-(2-aminoethoxy)ethyl]-2-methyl-1H-imidazo[4,5-c]quinolin-4-amine

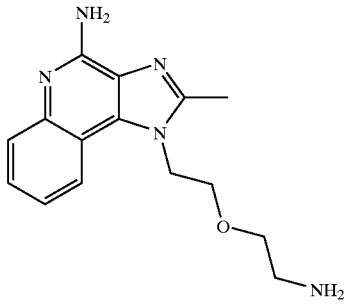

Part A

A solution of tert-butyl 2-{2-[(3-aminoquinolin-4-yl)amino]ethoxy}ethylcarbamate (12.05 g, 34.8 mmol) in 200 mL of 1,2-dichloroethane was treated with trimethyl orthoacetate (5.50 mL, 43.2 mmol) and the reaction mixture was heated to reflux. A 100 mg portion of pyridinium hydrochloride was then added and refluxing was continued for 4 h. The reaction was then cooled and washed with water and brine. The organic portion was dried over Na₂SO₄ and concentrated to give an orange foam. The foam was triturated with ether and filtered to yield 10.76 g of tert-butyl 2-[2-(2-methyl-1H-imidazo[4,5-c]quinolin-1-yl)ethoxy]ethylcarbamate as a tan solid.

Part B

A solution of tert-butyl 2-[2-(2-methyl-1H-imidazo[4,5-c]quinolin-1-yl)ethoxy]ethylcarbamate (10.75 g, 29.0 mmol) in 150 mL of CHCl₃ was chilled in an ice water bath. The solution was treated with 3-chloroperoxybenzoic acid (MCPBA, 70%, 10.73 g, 43.5 mmol). After stirring for 1.5 h, the reaction mixture was washed with 1% Na₂CO₃ (3×) solution and the layers were separated. The organic portion was washed with H₂O and brine then dried over Na₂SO₄ and concentrated to give a sticky brown solid. The solid was triturated with ether to yield 11.21 g of tert-butyl 2-[2-(2-methyl-5-oxido-1H-imidazo[4,5-c]quinolin-1-yl)ethoxy]ethylcarbamate as a light tan solid.

Part C

A solution of tert-butyl 2-[2-(2-methyl-5-oxido-1H-imidazo[4,5-c]quinolin-1-yl)ethoxy]ethylcarbamate (11.21 g, 29.0 mmol) in 75 mL of CH₂Cl₂ was treated with 75 mL of concentrated NH₄OH solution. The mixture was chilled in an ice water bath. To the rapidly stirred mixture was added solid p-toluenesulfonyl chloride (5.53 g, 29.0 mmol) over a 10 min period. The reaction mixture was then warmed to room temperature and treated with 75 mL of CH₂Cl₂ and 75 mL of water. The organic portion was then washed with 1% Na₂CO₃ solution (3×) and brine. The organic portion was dried over Na₂SO₄ and concentrated and triturated in ether to yield 7.13 g of tert-butyl 2-[2-(4-amino-2-methyl-1H-imidazo[4,5-c]quinolin-1-yl)ethoxy]ethylcarbamate as a light green solid.

Part D

Tert-butyl 2-[2-(4-amino-2-methyl-1H-imidazo[4,5-c]quinolin-1-yl)ethoxy]ethylcarbamate (7.13 g, 18.5 mmol) was suspended in 100 mL of 2M HCl in EtOH and the mixture was heated to reflux with stirring. After 3 h, the reaction mixture was chilled in an ice water bath and a filtered. The resulting solid was washed with small portions of ether to give the product as the hydrochloride salt. The free base was made by dissolving the hydrochloride salt in 100 mL of H$_2$O and treating with 20 mL of concentrated NH$_4$OH. The aqueous suspension was extracted with CH$_2$Cl$_2$ (3×75 mL). The combined organic layers were dried over Na$_2$SO$_4$ and concentrated to give 5.10 g of 1-[2-(2-aminoethoxy)ethyl]-2-methyl-1H-imidazo[4,5-c]quinolin-4-amineas a tan powder.

mp 155–157° C.; $^1$H NMR (300 MHz, DMSO-d$_6$) δ8.07 (d, J=7.5 Hz, 1 H), 7.61 (d, J=8.3 Hz, 1H), 7.41 (t, J=7.0 Hz, 1 H), 7.22 (t, J=8.1 Hz, 1 H), 6.50 (s, 2H), 4.70(t, J=5.2 Hz, 2 H), 3.85 (t, J=5.2 Hz, 2 H), 3.27 (t, J=5.4 Hz, 2 H), 3.03 (bs, 2 H), 2.61 (s, 3 H), 2.53 (t, J=5.6 Hz, 2 H); $^{13}$C NMR (75 MHz, DMSO-d$_6$) δ152.0, 150.9, 145.1, 132.8, 126.6, 121.3, 120.5, 115.1, 73.6, 69.4, 45.8, 41.6, 14.1; MS m/z 286 (M+H)$^+$; Anal. Calcd for C$_{15}$H$_{19}$N$_5$O: C, 63.14, H, 6.71, N, 24.54. Found: C, 62.74, H, 6.68, N, 24.55.

EXAMPLE 52

1-[2-(2-aminoethoxy)ethyl]-2-ethyl-1H-imidazo[4,5-c]quinolin-4-amine

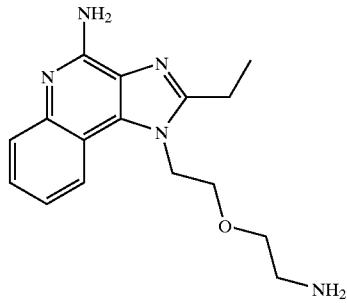

Part A

A solution of tert-butyl 2-{2-[(3-aminoquinolin-4-yl)amino]ethoxy}ethylcarbamate (32.0 g, 92.0 mmol) in 300 mL of CH$_2$Cl$_2$ was treated with triethylamine (19.2 mL, 138.0 mmol). The reaction was chilled in an ice water bath and then propionyl chloride (9.40 mL, 108.2 mmol) was added dropwise. After stirring for 18 h, the reaction was treated with water (150 mL) and the layers were separated. The aqueous portion was extracted with CH$_2$Cl$_2$ (3×50 mL). The combined organic portions were washed with 1% Na$_2$CO$_3$, water, brine, dried over Na$_2$SO$_4$, filtered and concentrated to yield a red sticky solid. The solid was triturated with ether and filtered to yield 16.5 g of tert-butyl 2-(2-{[3-(propionylamino)quinolin-4-yl]amino}ethoxy)ethylcarbamate as an off white powder.

Part B

A solution of tert-butyl 2-(2-{[3-(propionylamino)quinolin-4-yl]amino}ethoxy)ethylcarbamate (15.00 g, 37.3 mmol) in 200 mL of EtOH was treated with triethylamine (13.0 mL, 93.2 mmol). The reaction was heated to reflux with stirring. After 3 days, the reaction was concentrated, triturated with ether and filtered to yield 13.78 g of tert-butyl 2-[2-(2-ethyl-1H-imidazo[4,5-c]quinolin-1-yl)ethoxy]ethylcarbamate as an off white solid.

Part C

A solution of tert-butyl 2-[2-(2-ethyl-1H-imidazo[4,5-c]quinolin-1-yl)ethoxy]ethylcarbamate (13.78 g 35.8 mmol) in 175 mL of CHCl$_3$ was treated with 3-chloroperoxybenzoic acid (MCPBA, 70%, 10.28 g, 41.7 mmol). After stirring for 3 h, the reaction mixture was treated with water (100 mL) and CHCl$_3$ (50 mL) and the layers were separated. The organic portion was washed with 1% Na$_2$CO$_3$ solution (2×), water and brine then dried over Na$_2$SO$_4$ and concentrated to give 14.35 g tert-butyl 2-[2-(2-ethyl-5-oxido-1H-imidazo[4,5-c]quinolin-1-yl)ethoxy]ethylcarbamate as a sticky tan solid.

Part D

A solution of tert-butyl 2-[2-(2-ethyl-5-oxido-1H-imidazo[4,5-c]quinolin-1-yl)ethoxy]ethylcarbamate (14.3 g, 35.8 mmol) in 90 mL of CH$_2$Cl$_2$ was treated with 90 mL of concentrated NH$_4$OH solution. The mixture was chilled in an ice water bath. To the rapidly stirred mixture was added solid p-toluenesulfonyl chloride (7.05 g, 37.0 mmol) over a 10 min period. The reaction mixture was then warmed to room temperature. After 30 min, the reaction was treated with 90 mL of CH$_2$Cl$_2$ and 90 mL of water. The organic portion was then washed with 1% Na$_2$CO$_3$ solution (2×), water, brine, dried over Na$_2$SO$_4$ and concentrated. The resulting solid was triturated in ether and filtered to yield 9.35 g of tert-butyl 2-[2-(4-amino-2-ethyl-1H-imidazo[4,5-c]quinolin-1-yl)ethoxy]ethylcarbamate as a light tan solid.

Part E

Tert-butyl 2-[2-(4-amino-2-ethyl-1H-imidazo[4,5-c]quinolin-1-yl)ethoxy]ethylcarbamate (9.35 g, 23.4 mmol) was suspended in 150 mL of 2M HCl in EtOH and the mixture was heated to reflux with stirring. After 2 h, the reaction was cooled to room temperature and the HCl salt of the product was collected by vacuum filtration and rinsed with ether. The free base was made by dissolving the HCl salt in water and treating with 10% NaOH solution until the mixture was pH 12. The aqueous suspension was extracted with CH$_2$Cl$_2$ (10×50 mL). The combined organic layers were washed with brine, dried over Na$_2$SO$_4$ and concentrated to give 6.62 g of 1-[2-(2-aminoethoxy)ethyl]-2-ethyl-1H-imidazo[4,5-c]quinolin-4-amine as a light yellow solid. mp=144–146° C.; $^1$H NMR (300 MHz, DMSO-d$_6$) δ8.07 (d, J=7.5 Hz, 1 H), 7.61 (dd, J=1.0, 8.3 Hz, 1 H), 7.43–7.38 (m, 1 H), 7.25–7.17 (m, 1 H), 6.45 (s, 2 H), 4.71 (t, J=5.2 Hz, 2 H), 3.84 (t, J=5.2 Hz, 2 H), 3.27 (t, J=5.7 Hz, 2 H), 2.97 (q, J=7.5 Hz, 2 H), 2.51 (t, J=5.8 Hz, 2 H), 1.37 (t, J=7.5 Hz, 3 H), 1.25 (bs, 2 H); $^{13}$C NMR (75 MHz, DMSO-d$_6$) δ155.2, 152.1, 145.1, 132.8, 126.6, 126.6, 121.3, 120.5, 115.2, 73.8, 69.4, 45.4, 41.6, 20.4, 12.2; MS m/z 300 (M+H)$^+$; Anal. Calcd for C$_{16}$H$_{21}$N$_5$O: C, 64.19; H, 7.07; N, 23.39; Found: C, 63.98; H, 6.96; N, 23.27.

EXAMPLE 53

1-[2-(2-aminoethoxy)ethyl]-2-(ethoxymethyl)-1H-imidazo[4,5-c]quinolin-4-amine

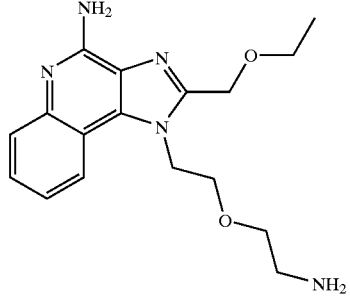

Part A

A solution of tert-butyl 2-{2-[(3-aminoquinolin-4-yl)amino]ethoxy}ethylcarbamate (18.04 g, 52.1 mmol) in 180 mL of pyridine was treated with 50 mg of 4-dimethylaminopyridine and chilled in an ice water bath. 2-ethoxyacetyl chloride (6.44 g, 52.6 mmol) was added dropwise to the solution. The reaction was stirred at room temperature for 3 h. The reaction was then heated to reflux with stirring. After 18 h the reaction was cooled and then concentrated. The residue was partitioned between CHCl$_3$ (150 mL) and water (150 mL) and the layers were separated. The aqueous portion was extracted with CHCl₃ (3×50 mL). The combined organic portions were washed with brine, dried over Na₂SO₄, filtered and concentrated to yield 15.47 g of tert-butyl 2-{2-[2-(ethoxymethyl)-1H-imidazo[4,5-c]quinolin-1-yl]ethoxy}ethylcarbamate as a sticky yellow solid.

Part B

A solution of tert-butyl 2-{2-[2-(ethoxymethyl)-1H-imidazo[4,5-c]quinolin-1-yl]ethoxy}ethylcarbamate (15.47 g, 37.3 mmol) in 150 mL of CHCl₃ was treated with 3-chloroperoxybenzoic acid (MCPBA, 70%, 15.12 g, 61.3 mmol). After stirring for 1.5 h, the reaction mixture was treated with water (100 mL) and CHCl₃ (50 mL) and the layers were separated. The organic portion was washed with 2% Na₂CO₃ solution (2×), H₂O and brine then dried over Na₂SO₄ and concentrated to give 16.06 g of tert-butyl 2-{2-[2-(ethoxymethyl)-5-oxido-1H-imidazo[4,5-c]quinolin-1-yl]ethoxy}ethylcarbamate as a yellow solid.

Part C

A solution of tert-butyl 2-{2-[2-(ethoxymethyl)-5-oxido-1H-imidazo[4,5-c]quinolin-1-yl]ethoxy}ethylcarbamate (16.06 g, 37.3 mmol) in 75 mL of CH₂Cl₂ was treated with 75 mL of concentrated NH₄OH solution. The mixture was chilled in an ice water bath. To the rapidly stirred mixture was added solid p-toluenesulfonyl chloride (7.82 g, 41.0 mmol) over a 10 min period. The reaction mixture was then warmed to room temperature. After 30 min, the reaction was treated with 75 mL of CH₂Cl₂ and 75 mL of water and the layers were separated. The organic portion was then washed with 1% Na₂CO₃ solution (2×), water, brine, dried over Na₂SO₄ and concentrated to give 14.95 g of tert-butyl 2-{2-[4-amino-2-(ethoxymethyl)-1H-imidazo[4,5-c]quinolin-1-yl]ethoxy}ethylcarbamate as a yellow solid.

Part D

Tert-butyl 2-{2-[4-amino-2-(ethoxymethyl)-1H-imidazo[4,5-c]quinolin-1-yl]ethoxy}ethylcarbamate (14.45 g, 33.6 mmol) was dissolved in 50 mL of 2M HCl in EtOH and the mixture was heated to reflux with stirring. After 3 h, the reaction was cooled to room temperature and treated with ether (100 mL). The HCl salt of the product was collected by vacuum filtration The free base was made by dissolving the hydrochloride salt in 75 mL of water and treating with concentrated NH₄OH until pH 12 was reached. The aqueous suspension was extracted with CH₂Cl₂ (4×50 mL). The combined organic layers were dried over Na₂SO₄ and concentrated to give a thick orange oil. The oil was dissolved in MeOH (100 mL), treated with 2 g of activated charcoal and heated to reflux. After 2 h, the mixture was filtered through a pad of Celite and rinsed with portions of MeOH. The filtrate was concentrated to yield 1-[2-(2-aminoethoxy)ethyl]-2-(ethoxymethyl)-1H-imidazo[4,5-c]quinolin-4-amine as a sticky orange solid.

MS 330 (M+H)⁺; ¹H NMR (300 MHz, DMSO-d₆) δ8.13 (d, J=8.1 Hz, 1 H), 7.62 (d, J=7.5 Hz, 1 H), 7.44 (m, 1 H), 7.25 (m, 1 H), 6.58 (s, 2 H), 4.85 (t, J=5.5 Hz, 2 H), 4.80 (s, 2 H), 3.86 (t, J=5.5 Hz, 2 H), 3.56 (q, J=7.0 Hz, 2 H), 3.30 (t, J=5.5 Hz, 2 H), 2.54 (t, J=5.6 Hz, 2 H), 1.17 (t, J=7.0 Hz, 3 H).

EXAMPLE 54

N-{2-[2-(4-amino-2-methyl-1H-imidazo[4,5-c]quinolin-1-yl)ethoxy]ethyl}methanesulfonamide

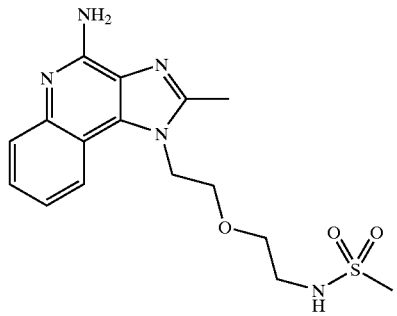

A solution of the compound of Example 51, 1-[2-(2-aminoethoxy)ethyl]-2-methyl-1H-imidazo[4,5-c]quinolin-4-amine (1.570 g, 5.50 mmol) in 40 mL of 1-methyl-2-pyrrolidinone was treated with triethylamine (1.53 mL, 11.0 mmol). With vigorous stirring, methanesulfonyl chloride (0.426 mL, 5.50 mmol) was added dropwise. After 18 h, the reaction was treated with 50 mL of water and then concentrated to yield a solid. The solid was purified by column chromatography (SiO₂, 90:10:0.5 CHCl₃:MeOH:NH₄OH) to yield 244 mg of N-{2-[2-(4-amino-2-methyl-1H-imidazo[4,5-c]quinolin-1-yl)ethoxy]ethyl}methanesulfonamide as a white solid.

mp=152–155° C.; ¹H NMR (300 MHz, DMSO-d₆) δ8.13 (d, J=7.9 Hz, 1 H), 7.68 (d, J=7.5 Hz, 1 H), 7.51 (t, J=7.2 Hz, 1 H), 7.34 (t, J=7.2 Hz, 1 H), 7.27 (s, 2 H), 7.02 (m, 1 H), 4.74 (t, J=5.0 Hz, 2 H), 3.89 (t, J=5.0 Hz, 2 H), 3.42 (t, J=5.7 Hz, 2 H), 3.02 (m, 2 H), 2.81 (s, 3 H), 2.65 (s, 3 H); ¹³C NMR (75 MHz, DMSO-d₆) δ152.2, 151.0, 141.3, 133.6, 127.6, 125.9, 124.0, 122.6, 121.0, 114.4, 70.2, 69.2, 45.9, 42.4, 14.2; MS m/z 364 (M+H)⁺; Anal. Calcd for C₁₆H₂₁N₅O₃S: C, 52.88; H, 5.82; N, 19.27; Found: C, 52.56; H, 5.75; N, 19.21.

EXAMPLE 55

N-{2-[2-(4-amino-2-methyl-1H-imidazo[4,5-c]quinolin-1-yl)ethoxy]ethyl}propane-2-sulfonamide

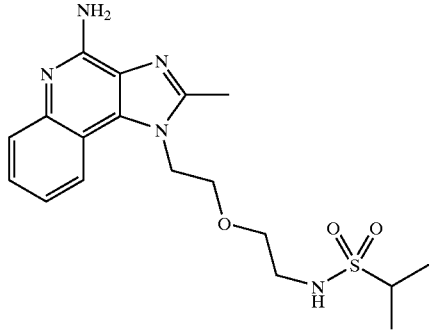

A solution of the compound of Example 51, 1-[2-(2-aminoethoxy)ethyl]-2-methyl-1H-imidazo[4,5-c]quinolin-4-amine (1.00 g, 3.50 mmol) in 30 mL of pyridine was chilled in an ice water bath. The stirred solution was treated dropwise with isopropylsulfonyl chloride (0.39 mL, 3.50 mmol) and the reaction was allowed to gradually warm to room temperature. After 18 h, the reaction was concentrated.

The crude product was purified by column chromatography (SiO$_2$, 90:10:0.5 CHCl$_3$:MeOH:NH$_4$OH) and then triturated in hexanes to give 314 mg of N-{2-[2-(4-amino-2-methyl-1H-imidazo[4,5-c]quinolin-1-yl)ethoxy]ethyl}propane-2-sulfonamide as a white solid.

mp=172–175° C.; $^1$H NMR (300 MHz, DMSO-d$_6$) δ 8.04 (d, J=7.5 Hz, 1 H), 7.62 (dd, J=1.1, 8.4 Hz, 1 H), 7.40 (m, 1 H), 7.22 (m, 1 H), 6.97 (t, J=5.2 Hz, 1 H), 6.48 (s, 2 H), 4.71 (t, J=5.2 Hz, 2 H), 3.88 (t, J=5.1 Hz, 2 H), 3.42–3.35 (m, 2 H), 3.07–2.95 (m, 3 H), 2.61 (s, 3 H), 1.11 (d, J=6.8 Hz, 6 H); $^{13}$C NMR (75 MHz, DMSO-d$_6$) δ 151.6, 150.5, 144.6, 132.3, 126.1, 120.9, 119.9, 114.7, 70.1, 68.9, 51.3, 45.3, 42.0, 16.1, 13.7; MS m/z 392 (M+H)$^+$; Anal. Calcd for C$_{18}$H$_{25}$N$_5$O$_3$S: C, 55.22; H, 6.44; N; 17.89. Found: C, 55.37; H, 6.52; N, 17.66.

EXAMPLE 56

N-{2-[2-(4-amino-2-ethyl-1H-imidazo[4,5-c]quinolin-1-yl)ethoxy]ethyl}methanesulfonamide

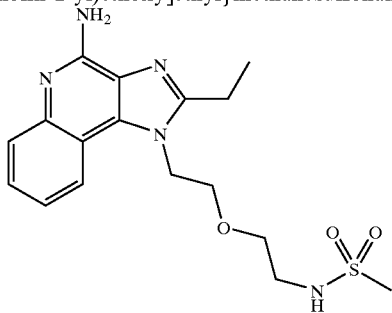

A solution of the compound of Example 52, 1-[2-(2-aminoethoxy)ethyl]-2-ethyl-1H-imidazo[4,5-c]quinolin-4-amine (800 mg, 2.67 mmol) in 30 mL of CH$_2$Cl$_2$ was treated with triethylamine (1.10 mL, 8.00 mmol). With vigorous stirring, the solution was treated dropwise with methanesulfonyl chloride (0.217 mL, 2.80 mmol). After 18 h, the reaction was treated with 50 mL of water and the layers were separated. The aqueous portion was extracted with CHCl$_3$ (3×30 mL). The combined organic portions were washed with brine, dried over Na$_2$SO$_4$, filtered and concentrated to yield an off white solid. Purification by column chromatography (SiO$_2$, 95:5:0.5 CHCl$_3$:MeOH:NH$_4$OH) gave 463 mg of N-{2-[2-(4-amino-2-ethyl-1H-imidazo[4,5-c]quinolin-1-yl)ethoxy]ethyl}methanesulfonamide as a white solid.

mp=169–171° C.; $^1$H NMR (300 MHz, DMSO-d$_6$) δ 8.05 (d, J=7.5 Hz, 1 H), 7.62 (dd, J=1.1, 7.3 Hz, 1 H), 7.45–7.37 (m, 1 H), 7.22 (m, 1 H), 7.03–6.95 (m, 1 H), 6.44 (s, 2 H), 4.71 (t, J=5.3 Hz, 2 H), 3.87 (t, J=5.2 Hz, 2 H), 3.40 (t, J=5.9 Hz, 2 H), 3.05–2.95 (m, 4 H), 2.81 (s, 3 H), 1.38 (t, J=7.4 Hz, 3 H); $^{13}$C NMR (75 MHz, DMSO-d$_6$) δ 155.2, 152.1, 132.8, 126.6, 121.4, 120.5, 115.2, 70.2, 69.3, 45.3, 42.4, 20.4, 12.2; MS m/z 378 (M+H)$^+$; Anal. Calcd for C$_{17}$H$_{23}$N$_5$O$_3$S: C, 54.09; H, 6.14; N, 18.55; Found: C, 54.16; H, 6.25; N, 18.37.

EXAMPLE 57

N-(2-{2-[4-amino-2-(ethoxymethyl)-1H-imidazo[4,5-c]quinolin-1-yl]ethoxy}ethyl)methanesulfonamide

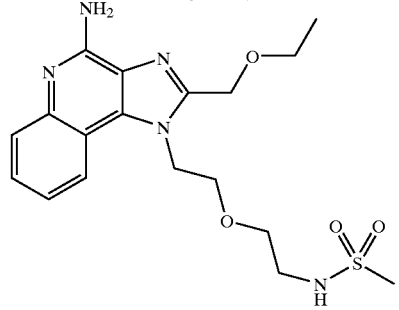

A solution of the compound of Example 53, 1-[2-(2-aminoethoxy)ethyl]-2-(ethoxymethyl)-1H-imidazo[4,5-c]quinolin-4-amine (980 mg, 2.98 mmol) in 20 mL of CH$_2$Cl$_2$ was treated with triethylamine (1.04 mL, 7.45 mmol) and chilled in an ice water bath. With vigorous stirring, the solution was treated dropwise with methanesulfonyl chloride (0.242 mL, 3.13 mmol). After 18 h, the reaction was treated with 40 mL CH$_2$Cl$_2$, 20 mL CHCl$_3$, 25 mL water and the layers were separated. The organic portion was washed with 1% Na$_2$CO$_3$ solution, water and brine. The organic portion was then dried over Na$_2$SO$_4$, filtered and concentrated to yield a yellow foam. Purification by column chromatography (SiO$_2$, 90:10:0.5 CHCl$_3$:MeOH:NH$_4$OH) followed by recrystallization from CH$_2$Cl$_2$ gave 282 mg of N-(2-{2-[4-amino-2-(ethoxymethyl)-1H-imidazo[4,5-c]quinolin-1-yl]ethoxy}ethyl)methanesulfonamide as light yellow crystals.

mp=152–155° C.; $^1$H NMR (300 MHz, DMSO-d$_6$) δ 8.09 (d, J=7.4 Hz, 1 H), 7.63 (dd, J=1.1, 8.4 Hz, 1 H), 7.44 (m, 1 H), 7.25 (m, 1 H), 7.01 (t, J=5.5 Hz, 1 H), 6.58 (s, 2 H), 4.83 (t, J=5.5 Hz, 2 H), 4.81 (s, 2 H), 3.87 (t, J=5.5 Hz, 2 H), 3.55 (q, J=7.0 Hz, 2 H), 3.42 (t, J=5.5 Hz, 2 H), 3.02 (t, J=5.5 Hz, 2 H), 2.82 (s, 3 H), 1.17 (t, J=6.9 Hz, 3 H); $^{13}$C NMR (75 MHz, DMSO-d$_6$) δ 152.3, 149.9, 145.6, 133.5, 127.2, 126.7, 121.5, 120.8, 115.0, 70.2, 69.3, 65.7, 64.8, 45.6, 42.4, 15.3; MS m/z 408 (M+H)$^+$; Anal. Calcd for C$_{18}$H$_{25}$N$_5$O$_4$S: C, 53.06; H, 6.18; N, 17.19; Found: C, 52.84; H, 5.84; N, 17.14.

EXAMPLE 58

N-(2-{2-[4-amino-2-(ethoxymethyl)-1H-imidazo[4,5-c]quinolin-1-yl]ethoxy}ethyl)propane-2-sulfonamide

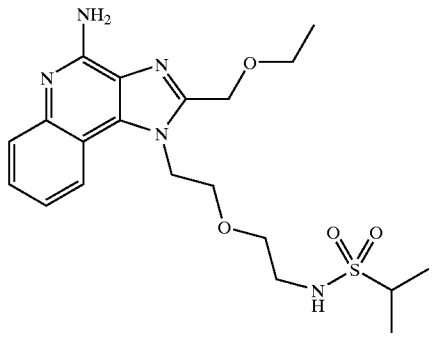

A solution of the compound of Example 53, 1-[2-(2-aminoethoxy)ethyl]-2-(ethoxymethyl)-1H-imidazo[4,5-c]

quinolin-4-amine (980 mg, 2.98 mmol) in 20 mL CH$_2$Cl$_2$ was treated with triethylamine (1.04 mL, 7.45 mmol) and chilled in an ice water bath. With vigorous stirring, the solution was treated dropwise with isopropylsulfonyl chloride (0.351 mL, 3.13 mmol). After 18 h, the reaction was treated with 25 mL CH$_2$Cl$_2$ and 25 mL water and the layers were separated. The organic portion was washed with 1% Na$_2$CO$_3$ solution, water, brine, dried over Na$_2$SO$_4$, filtered and concentrated to yield a yellow foam. Purification by column chromatography (SiO$_2$, 90:10:0.5 CHCl$_3$:MeOH:NH$_4$OH) followed by recrystallization from CH$_2$Cl$_2$/hexanes gave 308 mg of N-(2-{2-[4-amino-2-(ethoxymethyl)-1H-imidazo[4,5-c]quinolin-1-yl]ethoxy}ethyl)propane-2-sulfonamide as a light yellow solid. mp=139–142° C.; $^1$H NMR (300 MHz, DMSO-d$_6$) δ8.09 (d, J=7.7 Hz, 1 H), 7.63 (dd, J=1.0, 8.3 Hz, 1 H), 7.44 (m, 1 H), 7.26 (m, 1 H), 6.98 (t, J=5.6 Hz, 1 H), 6.58 (s, 2 H), 4.82 (t, J=5.5 Hz, 2 H), 4.81 (s, 2 H), 3.88 (t, J=5.5 Hz, 2 H), 3.55 (q, J=7.0 Hz, 2 H), 3.40 (t, J=5.7 Hz, 2 H), 3.06–2.96 (m, 3 H), 1.17 (t, J=7.0 Hz, 3 H), 1.11 (d, J=6.7 Hz, 6 H); $^{13}$C NMR (75 MHz, DMSO-d$_6$) δ152.3, 149.9, 145.6, 133.5, 127.2, 126.6, 121.5, 120.8, 115.0, 70.5, 69.3, 65.7, 64.8, 51.7, 45.6, 42.4, 16.5, 15.3; MS m/z 436 (M+H)$^+$;

Anal. Calcd for C$_{20}$H$_{29}$N$_5$O$_4$S: C, 55.15; H, 6.71; N, 16.08; Found: C, 55.00; H, 6.77; N 16.04.

EXAMPLE 59

N-(2-{2-[4-amino-2-(2-methoxyethyl)-1H-imidazo[4,5-c]quinolin-1-yl]ethoxy}ethyl)-N-methylpropane-2-sulfonamide

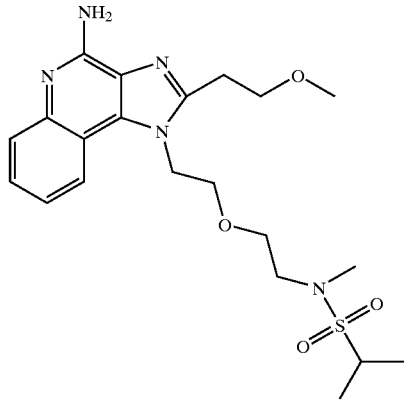

2-(2-Methoxyethyl)-1-{2-[2-(methylamino)ethoxy]ethyl}-1H-imidazo[4,5-c]quinolin-4-amine (965 mg, 2.81 mmol) was dissolved in 30 mL of anhydrous CH$_2$Cl$_2$ and cooled to 0° C. under N$_2$. To the stirred solution were added Et$_3$N (0.78 mL, 5.63 mmol) and isopropylsulfonyl chloride (316 μL, 2.81 mmol) and the reaction was allowed to warm to room temperature overnight. The reaction mixture was then quenched by addition of saturated NaHCO$_3$ solution (30 mL) and CH$_2$Cl$_2$ (30 mL). The organic layer was separated and washed with H$_2$O and brine, dried over Na$_2$SO$_4$ and concentrated under reduced pressure. Column chromatography (3% MeOH/CHCl$_3$ saturated with NH$_4$OH) gave 0.28 g of sticky solid. Crystallization from EtOAc/CH$_2$Cl$_2$ gave 120 mg of N-(2-{2-[4-amino-2-(2-methoxyethyl)-1H-imidazo[4,5-c]quinolin-1-yl]ethoxy}ethyl)-N-methylpropane-2-sulfonamide as amber crystals. m.p. 129.7–130.2° C.; MS m/z 450 (M+H)$^+$; $^1$H NMR (300 MHz, d$_6$-DMSO) ∝8.07 (d, J=7.6 Hz, 1H); 7.61 (dd, J=1.1, 8.3 Hz, 1H); 7.41 (ddd, J=1.1, 7.0, 8.1 Hz, 1H); 7.23 (ddd, J=1.2, 6.9, 8.2 Hz, 1H); 6.47 (s, 2H); 4.77 (t, J=5.0 Hz, 2H); 3.87 (t, J=5.0 Hz, 2H), 3.83 (t, J=6.8 Hz, 2H); 3.47 (t, J=5.4 Hz, 2H); 3.30 (s, 3H); 3.23–3.13 (m, 5H); 2.69 (s, 3H); 1.07 (d, J=6.8 Hz, 6H); $^{13}$C NMR (75 MHz, d$_6$-DMSO) ∝152.0, 151.8, 145.2, 132.7, 126.7, 121.4, 120.6, 115.1, 70.4, 69.6, 69.3, 58.5, 52.0, 49.2, 45.4, 35.7, 27.7, 16.6. Anal. Calcd for C$_{21}$H$_{31}$N$_5$O$_4$S: C, 56.10; H, 6.95 ; N, 15.58. Found: C, 56.25 ; H, 6.89 ; N, 15.51.

EXAMPLE 60

1-{2-[2-(1,1-Dioxidoisothiazolidin-2-yl)ethoxy]ethyl}-2-methyl-1H-imidazo[4,5-c]quinolin-4-amine.

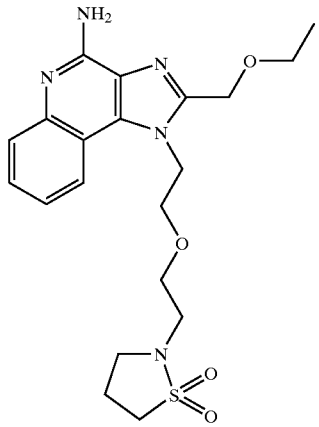

Using the general method of Example 5, chloropropylsulfonyl chloride (0.13 ml, 1.05 mmol) was reacted with 1-[2-(2-aminoethoxy)ethyl]-2-methyl-1H-imidazo[4,5-c]quinolin-4-amine (0.3 g, 1.05 mmol). Recrystallization from 2-propanol yielded 0.2 g of 1-{2-[2-(1,1-dioxidoisothiazolidin-2-yl)ethoxy]ethyl}-2-methyl-1H-imidazo[4,5-c]quinolin-4-amine as an off-white powder, m.p. 186.0–187.0° C.

$^1$H NMR (300 MHz, DMSO-d$_6$) δ8.06 (d, J=7.6 Hz, 1 H), 7.61 (dd, J=8.3, 1.0 Hz, 1 H), 7.41 (dt, J=7.6, 1.0 Hz, 1 H), 7.23 (dt, J=7.6, 1.2 Hz, 1 H), 6.56 (s, 2 H), 4.72 (t, J=5.0 Hz, 2 H), 3.87 (t, J=5.0 Hz, 2 H), 3.46 (t, J=5.3 Hz, 2 H), 3.07 (t, J=7.7 Hz, 2 H), 2.95–2.86 (m, 4 H), 2.61 (s, 3 H), 2.03 (quintet, J=6.9 Hz, 2 H);

$^{13}$C NMR (75 Hz, DMSO-d$_6$) δ151.5,150.8, 144.4, 132.5, 126.3, 126.1, 126.0, 121.0, 120.2, 114.7, 68.9, 46.9, 45.5, 45.3, 43.7, 18.2, 13.7;

MS (CI) m/e 390.1607 (390.1600 calcd for C$_{18}$H$_{23}$N$_5$O$_3$S, M+H).

Anal calcd for C$_{18}$H$_{23}$N$_5$O$_3$S: %C, 55.51; %H, 5.95; %N, 17.98; %S, 8.23. Found: %C, 55.26; %H, 5.87; %N, 17.87; %S, 8.13.

Cytokine Induction in Human Cells

An in vitro human blood cell system is used to assess cytokine induction. Activity is based on the measurement of interferon and tumor necrosis factor (α) (IFN and TNF, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using Histopaque®-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at $4 \times 10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30–0.014 $\mu$M.

Incubation

The solution of test compound is added at 60 $\mu$M to the first well containing RPMI complete and serial 3 fold dilutions are made in the wells. The PBMC suspension is then added to the wells in an equal volume, bringing the test compound concentrations to the desired range (30–0.014 $\mu$M). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (~200×g) at 4° C. The cell-free culture supernatant is removed with a sterile polypropylene pipet and transferred to sterile polypropylene tubes. Samples are maintained at −30 to −70° C. until analysis. The samples are analyzed for interferon ($\alpha$) by ELISA and for tumor necrosis factor ($\alpha$) by ELISA or IGEN Assay Interferon ($\alpha$) and Tumor Necrosis Factor ($\alpha$) Analysis by ELISA Interferon ($\alpha$) concentration is determined by ELISA using a Human Multi-Species kit from PBL Biomedical Laboratories, New Brunswick, N.J. Results are expressed in pg/mL.

Tumor necrosis factor ($\alpha$) (TNF) concentration is determined using ELISA kits available from Biosource International, Camarillo, Calif. Alternately, the TNF concentration can be determined by Origen® M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

The table below lists the lowest concentration found to induce interferon and the lowest concentration found to induce tumor necrosis factor for each compound. A "*" indicates that no induction was seen at any of the concentrations; generally the highest concentration tested was 10 or 30 $\mu$M.

| | Cytokine Induction in Human Cells | |
|---|---|---|
| Example | Lowest Effective Concentration ($\mu$M) | |
| Number | Interferon | Tumor Necrosis Factor |
| 3 | 0.01 | 0.12 |
| 6 | 0.001 | 1 |
| 7 | 0.01 | 1 |
| 8 | 0.01 | 1 |

| | -continued | |
|---|---|---|
| | Cytokine Induction in Human Cells | |
| Example | Lowest Effective Concentration ($\mu$M) | |
| Number | Interferon | Tumor Necrosis Factor |
| 9 | 0.1 | 1 |
| 10 | 1 | 10 |
| 11 | 1 | 10 |
| 12 | 0.1 | 10 |
| 13 | 1 | 10 |
| 14 | 1 | 10 |
| 15 | 10 | 10 |
| 16 | 1 | 10 |
| 17 | 1 | 10 |
| 18 | * | 10 |
| 19 | * | 10 |
| 20 | 1 | 10 |
| 21 | 10 | 10 |
| 22 | 0.0001 | 10 |
| 23 | 0.0001 | 10 |
| 24 | 0.0001 | 10 |
| 25 | 0.0001 | * |
| 26 | 0.01 | 10 |
| 27 | 0.1 | 1 |
| 28 | 0.1 | 1 |
| 29 | 1 | 10 |
| 30 | 1 | 10 |
| 31 | 1 | 10 |
| 32 | 1 | 1 |
| 33 | 1 | 1 |
| 34 | 1 | 1 |
| 35 | 1 | 1 |
| 36 | 1 | 10 |
| 37 | 0.1 | 1 |
| 38 | * | * |
| 39 | 1 | * |
| 41 | 10 | 1 |
| 42 | 10 | 1 |
| 43 | 10 | 10 |
| 44 | 1 | 10 |
| 45 | * | * |
| 46 | * | * |
| 47 | * | * |
| 48 | * | 10 |
| 49 | * | 10 |
| 50 | 1.11 | * |

What is claimed is:
1. A compound of the formula (I):

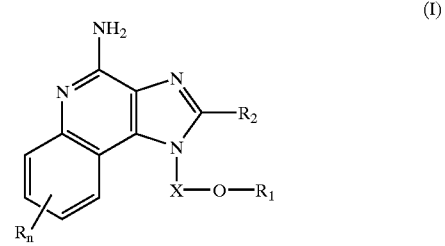

wherein:
X is —CHR$_5$—, —CHR$_5$-alkyl-, or —CHR$_5$-alkenyl-;
R$_1$ is selected from the group consisting of:
—R$_4$—NR$_3$—SO$_2$—R$_6$-alkyl;
—R$_4$—NR$_3$—SO$_2$—R$_6$-alkenyl;
—R$_4$—NR$_3$—SO$_2$—R$_6$-aryl;
—R$_4$—NR$_3$—SO$_2$—R$_6$-heteroaryl;
—R$_4$—NR$_3$—SO$_2$—R$_6$-heterocyclyl;
—R$_4$—NR$_3$—SO$_2$—R$_7$;
—R$_4$—NR$_3$—SO$_2$—NR$_5$—R$_6$-alkyl;
—R$_4$—NR$_3$—SO$_2$—NR$_5$—R$_6$-alkenyl;

—R$_4$—NR$_3$—SO$_2$—NR$_5$—R$_6$-aryl;
—R$_4$—NR$_3$—SO$_2$—NR$_5$—R$_6$-heteroaryl;
—R$_4$—NR$_3$—SO$_2$—NR$_5$—R$_6$-heterocyclyl; and
—R$_4$—NR$_3$—SO$_2$—NR$_2$;

R$_2$ is selected from the group consisting of:
  -hydrogen;
  -alkyl;
  -alkenyl;
  -aryl;
  -heteroaryl;
  -heterocyclyl;
  -alkyl-Y-alkyl;
  -alkyl-Y-alkenyl;
  -alkyl-Y-aryl; and
  -alkyl or alkenyl substituted by one or more substituents selected from the group consisting of:
    —OH;
    -halogen;
    —N(R$_5$)$_2$;
    —CO—N(R$_5$)$_2$;
    —CO—C$_{1-10}$ alkyl;
    —CO—O—C$_{1-10}$ alkyl;
    —N$_3$;
    -aryl;
    -heteroaryl;
    -heterocyclyl;
    —CO-aryl; and
    —CO-heteroaryl;

Y is —O— or —S(O)$_{0-2}$—;
R$_3$ is H, C$_{1-10}$ alkyl, or arylalkyl;
each R$_4$ is independently alkyl or alkenyl, which may be interrupted by one or more —O— groups; or when R$_3$ is C$_{1-10}$ alkyl R$_3$ and R$_4$ can join together to form a piperidine ring;
each R$_5$ is independently H, C$_{1-10}$ alkyl, or C$_{2-10}$ alkenyl;
R$_6$ is a bond, alkyl, or alkenyl, which may be interrupted by one or more —O— groups;
R$_7$ is C$_{1-10}$ alkyl; or when R$_3$ is C$_{1-10}$ alkyl R$_3$ and R$_7$ can join together to form a 5-membered heterocyclic ring;
n is 0; and
each R present is independently selected from the group consisting of C$_{1-10}$ alkyl,
C$_{1-10}$ alkoxy, hydroxy, halogen and trifluoromethyl;
or a pharmaceutically acceptable salt thereof.

2. A compound or salt of claim 1 wherein X is —CH(alkyl)-alkyl-, wherein the alkyl groups can be the same or different.

3. A compound or salt of claim 1 wherein X is —CH$_2$—CH$_2$—.

4. A compound or salt of claim 1 wherein X is —CH(C$_2$H$_5$)—CH$_2$—.

5. A compound or salt of claim 1 wherein R$_2$ is H.

6. A compound or salt of claim 1 wherein R$_2$ is alkyl.

7. A compound or salt of claim 1 wherein R$_2$ is -alkyl-O-alkyl.

8. A compound or salt of claim 1 wherein R$_3$ and R$_4$ join to form a piperidine ring.

9. A compound or salt of claim 1 wherein R$_1$ is —R$_4$—NR$_3$—SO$_2$—R$_6$-aryl.

10. A compound selected from the group consisting of:
N-(2-{2-[4-amino-2-(2-methoxyethyl)-1H-imidazo[4,5-c]quinolin-1-yl]ethoxy}ethyl)-N-methylpropane-2-sulfonamide;

N-{2-[2-(4-amino-2-ethyl-1H-imidazo[4,5-c]quinolin-1-yl) ethoxy]ethyl}methanesulfonamide;

N-{2-[2-(4-amino-2-methyl-1H-imidazo[4,5-c]quinolin-1-yl) ethoxy]ethyl}methanesulfonamide; and N-{2-[2-(4-amino-2-methyl-1H-imidazo[4,5-c]quinolin-1-yl) ethoxy]ethyl}propane-2-sulfonamide;

or a pharmaceutically acceptable salt thereof.

11. A compound of the formula (II)

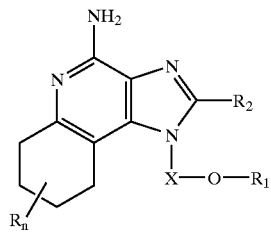

(II)

wherein:
X is —CHR$_5$—, —CHR$_5$-alkyl-, or —CHR$_5$-alkenyl-;
R$_1$ is selected from the group consisting of:
  —R$_4$—NR$_3$—SO$_2$—R$_6$-alkyl;
  —R$_4$—NR$_3$—SO$_2$—R$_6$-alkenyl;
  —R$_4$—NR$_3$—SO$_2$—R$_6$-aryl;
  —R$_4$—NR$_3$—SO$_2$—R$_6$-heteroaryl;
  —R$_4$—NR$_3$—SO$_2$—R$_6$-heterocyclyl;
  —R$_4$—NR$_3$—SO$_2$—R$_7$;
  —R$_4$—NR$_3$—SO$_2$—NR$_5$—R$_6$-alkyl;
  —R$_4$—NR$_3$—SO$_2$—NR$_5$—R$_6$-alkenyl;
  —R$_4$—NR$_3$—SO$_2$—NR$_5$—R$_6$-aryl;
  —R$_4$—NR$_3$—SO$_2$—NR$_5$—R$_6$-heteroaryl;
  —R$_4$—NR$_3$—SO$_2$—NR$_5$—R$_6$-heterocyclyl; and
  —R$_4$—NR$_3$—SO$_2$—NH$_2$;

R$_2$ is selected from the group consisting of:
  -hydrogen;
  -alkyl;
  -alkenyl;
  -aryl;
  -heteroaryl;
  -heterocyclyl;
  -alkyl-Y-alkyl;
  -alkyl-Y-alkenyl;
  -alkyl-Y-aryl; and
  -alkyl or alkenyl substituted by one or more substituents selected from the group consisting of:
    —OH;
    -halogen;
    —N(R$_5$)$_2$;
    —CO—N(R$_5$)$_2$;
    —CO—C$_{1-10}$ alkyl;
    —CO—O—C$_{1-10}$ alkyl;
    —N$_3$;
    -aryl;
    -heteroaryl;
    -heterocyclyl;
    —CO—aryl; and
    —CO—heteroaryl;

Y is —O— or —S(O)$_{0-2}$—;
R$_3$ is H, C$_{1-10}$ alkyl, or arylalkyl;
each R$_4$ is independently alkyl or alkenyl, which may be interrupted by one or more —O— groups; or when R$_3$ is C$_{1-10}$ alkyl R$_3$ and R$_4$ can join together to form a piperidine ring;
each R$_5$ is independently H, C$_{1-10}$ alkyl, or C$_{2-10}$ alkenyl;
R$_6$ is a bond, alkyl, or alkenyl, which may be interrupted by one or more —O— groups;

$R_7$ is $C_{1-10}$ alkyl; or when $R_3$ is $C_{1-10}$ alkyl $R_3$ and $R_7$ can join together to form a 5-membered heterocyclic ring;

n is 0; and each R present is independently selected from the group consisting of $C_{1-10}$ alkyl, $C_{1-10}$ alkoxy, hydroxy, halogen, and trifluoromethyl;

or a pharmaceutically acceptable salt thereof.

12. A compound or salt of claim 11 wherein $R_2$ is H or alkyl.

13. A compound or salt of claim 11 wherein $R_2$ is -alkyl-O-alkyl.

14. A pharmaceutical composition comprising a therapeutically effective amount of a compound or salt of claim 1 and a pharmaceutically acceptable carrier.

15. A method of inducing cytokine biosynthesis in an animal comprising administering a compound or salt of claim 1 to the animal in an amount effective for cytokine induction.

16. The method of claim 15 wherein the cytokine is IFN-α.

17. A method of treating a viral disease in an animal comprising administering to the animal a therapeutically effective amount of a compound of claim 1 that induces cytokine biosynthesis.

18. A compound of the formula (III):

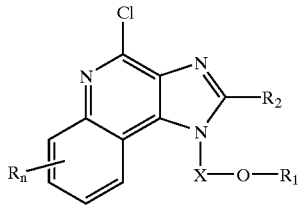

(III)

wherein

X is —$CHR_5$—, —$CHR_5$-alkyl-, or —$CHR_5$-alkenyl-;

$R_1$ is selected from the group consisting of:
 —$R_4$—$NR_3$—$SO_2$—$R_6$-alkyl;
 —$R_4$—$NR_3$—$SO_2R_6$-alkenyl;
 —$R_4$—$NR_3$—$SO_2$—$R_6$-aryl;
 —$R_4$—$NR_3$—$SO_2$—$R_6$-heteroaryl;
 —$R_4$—$NR_3$—$SO_2$—$R_6$-heterocyclyl;
 —$R_4$—$NR_3$—$SO_2$—$R_7$;
 —$R_4$—$NR_3$—$SO_2$—$NR_5$—$R_6$-alkyl;
 —$R_4$—$NR_3$—$SO_2$—$NR_5$—$R_6$-alkenyl;
 —$R_4$—$NR_3$—$SO_2$—$NR_5$—$R_6$-aryl;
 —$R_4$—$NR_3$—$SO_2$—$NR_5$—$R_6$-heteroaryl;
 —$R_4$—$NR_3$—$SO_2$—$NR_5$—$R_6$-heterocyclyl; and
 —$R_4$—$NR_3$—$SO_2$—$NH_2$;

$R_2$ is selected from the group consisting of:
 -hydrogen;
 -alkyl;
 -alkenyl;
 -aryl;
 -heteroaryl;
 -heterocyclyl;
 -alkyl-Y-alkyl;
 -alkyl-Y-alkenyl;
 -alkyl-Y-aryl; and
 -alkyl or alkenyl substituted by one or more substituents selected from the group consisting of:
  —OH;
  -halogen;
  —$N(R_5)_2$;
  —CO—$N(R_5)_2$;
  —CO—$C_{1-10}$ alkyl;
  —CO—O—$C_{1-10}$ alkyl;
  —$N_3$;
  -aryl;
  -heteroaryl;
  -heterocyclyl;
  —CO—aryl; and
  —CO—heteroaryl;

Y is —O— or —$S(O)_{0-2}$;

$R_3$ is H, $C_{1-10}$ alkyl, or arylalkyl;

each $R_4$ is independently alkyl or alkenyl, which may be interrupted by one or more —O— groups; or when $R_3$ is $C_{1-10}$ alkyl $R_4$ and $R_3$ can join to form a piperidine ring;

each $R_5$ is independently H, $C_{1-10}$ alkyl, or $C_{2-10}$ alkenyl;

$R_6$ is a bond, or is alkyl or alkenyl, which may be interrupted by one or more —O— groups;

$R_7$ is $C_{1-10}$ alkyl; or when $R_3$ is $C_{1-10}$ alkyl $R_3$ and $R_7$ can join together to form a 5-membered heterocyclic ring;

n; and each R present is independently selected from the group consisting of $C_{1-10}$ alkyl, $C_{1-10}$ alkoxy, hydroxy, halogen and trifluoromethyl;

or a pharmaceutically acceptable salt thereof.

19. A pharmaceutical composition comprising a therapeutically effective amount of a compound or salt of claim 11 and a pharmaceutically acceptable carrier.

20. A method of inducing cytokine biosynthesis in an animal comprising administering a compound or salt of claim 11 to the animal in an amount effective for cytokine induction.

21. The method of claim 20 wherein the cytokine is IFN-α.

22. A method of treating a viral disease in an animal comprising administering to the animal a therapeutically effective amount of a compound of claim 11 that induces cytokine biosynthesis.

23. The method according to claim 15 wherein the animal has a viral disease.

24. The method according to claim 15 wherein the animal has a neoplastic disease.

25. The method according to claim 20 wherein the animal has a viral disease.

26. The method according to claim 20 wherein the animal has a neoplastic disease.

* * * * *

UNITED STATES PATENT AND TRADEMARK OFFICE
CERTIFICATE OF CORRECTION

PATENT NO. : 6,677,347 B2
DATED : January 13, 2004
INVENTOR(S) : Crooks, Stephen L.

It is certified that error appears in the above-identified patent and that said Letters Patent is hereby corrected as shown below:

Title page,
Item [63], Related U.S. Application Data, please delete "Dec. 1" and insert -- Dec. 6 --, therefore.

Column 1,
Line 5, please delete "Dec. 1" and insert -- Dec. 6 --, therefore.

Column 18,
Line 55, after "groups" insert -- . --.

Column 20,
Line 5, after "indirectly" delete ",".

Column 24,
Line 8, please delete "methanesulfoneamide" and insert -- methanesulfonamide --, therefore.

Column 27,
Line 36, please delete "(t, J=5.6 Hz, 2)" and insert -- (t, J=5.6 Hz, 2H) --.

Column 29,
Line 11, please delete "$C_{19}H_{27}N_5O_4S.0.40$" and insert -- $C_{19}H_{27}N_5O_4S \bullet 0.40$ --, therefore.

Column 30,
Line 11, please delete "concetrated" and insert -- concentrated --, therefore.

Column 71,
Line 49, after "filtration" insert -- . --.

Column 77,
Line 34, after "Assay" insert -- . --.

UNITED STATES PATENT AND TRADEMARK OFFICE
CERTIFICATE OF CORRECTION

PATENT NO. : 6,677,347 B2
DATED : January 13, 2004
INVENTOR(S) : Crooks, Stephen L.

It is certified that error appears in the above-identified patent and that said Letters Patent is hereby corrected as shown below:

Column 79,
Line 47, delete "-alkyl-" and insert -- (alkyl)- --, therefore.

Column 82,
Line 31, after "n" insert -- is 0 --.

Signed and Sealed this

Seventeenth Day of August, 2004

JON W. DUDAS
*Acting Director of the United States Patent and Trademark Office*